United States Patent
Ito

(10) Patent No.: US 9,593,147 B2
(45) Date of Patent: Mar. 14, 2017

(54) IGA-BINDING PEPTIDE AND PURIFICATION OF IGA USING THE SAME

(75) Inventor: Yuji Ito, Kagoshima (JP)

(73) Assignees: Kagoshima University, Kagoshima (JP); Otsuka Chemical Co., Ltd., Osaka (JP)

( * ) Notice: Subject to any disclaimer, the term of this patent is extended or adjusted under 35 U.S.C. 154(b) by 922 days.

(21) Appl. No.: 13/699,579

(22) PCT Filed: May 24, 2011

(86) PCT No.: PCT/JP2011/061906
§ 371 (c)(1),
(2), (4) Date: Nov. 21, 2012

(87) PCT Pub. No.: WO2011/148952
PCT Pub. Date: Dec. 1, 2011

(65) Prior Publication Data
US 2013/0078741 A1  Mar. 28, 2013

(30) Foreign Application Priority Data
May 24, 2010  (JP) .................................. 2010-118508

(51) Int. Cl.
| | | |
|---|---|---|
| C07K 7/08 | (2006.01) | |
| G01N 33/68 | (2006.01) | |
| C07K 16/06 | (2006.01) | |
| B01D 15/38 | (2006.01) | |
| B01J 20/286 | (2006.01) | |
| G01N 30/88 | (2006.01) | |

(52) U.S. Cl.
CPC ............ *C07K 7/08* (2013.01); *B01D 15/3809* (2013.01); *B01J 20/286* (2013.01); *C07K 16/065* (2013.01); *G01N 33/6854* (2013.01); *C07K 2317/21* (2013.01); *G01N 2030/8831* (2013.01)

(58) Field of Classification Search
None
See application file for complete search history.

(56) References Cited

U.S. PATENT DOCUMENTS

2003/0091565 A1* 5/2003 Beltzer et al. ............ 424/144.1
2010/0297606 A1  11/2010 Ito

FOREIGN PATENT DOCUMENTS

WO   WO-00/63383 A1   10/2000
WO   WO-2008/054030 A1   5/2008

OTHER PUBLICATIONS

Hatanaka et al. "Isolation and characterization of huam IgA-specific binding peptides from random peptide library on T7 phage display system," Peptide Science 2010: Proceedings of the 5th International Peptide Symposium in Conjunction with the 47th Japanese Peptide Symposium, Dec. 4-9, 2010, Kyoto International Conference Center, Kyoto Japan.*
Sakamoto et al. "Discovery and characterization of a peptide motif that specifically recognizes a non-native conformation of human IgG induced by acidic pH conditions." J Biol Chem. Apr. 10, 2009;284(15):9986-93.*
Hatanakna, T. et al., Affinity purification of IgG by specific peptide-conjugated column., Dai 46 Kai Peptide Toronkai Koen Yoshishu, 2009, vol. 46th, p. 103,P-059.
Sakamoto, K. et al., Discovery and Charaterization of a Peptide Motif That Specifically Recognizes a Non-native Conformation of Human IgG Induced by Acidic pH Conditions., J. Biol. Chem., 2009, vol. 284, No. 15, p. 9986-9993.
Sandin, C. et al., Isolation and Detection of Human IgA Using a *Streptococcal* IgA-Binding Peptide., J. Immunol., 2002, vol. 169, p. 1357-1364.
Yuji Ito, "Peptide ni yoru Shinki Hito Kotai no Kenshutsu Sieiseiho no Kaihatsu", [online], Ikusei Kenkyu: JST Innovation Satellite Miyazaki Heisei 18 Nendo Saitaku Kadai'Seigyogata Hito Kotai Ketsugo Peptide ni yoru Kotai no Kenshutsu, Seisei Gijutsu no Kaihatsu', 2009 [retrieval date Jun. 15, 2011].
PCT/JP2011/061906 International Search Report.

\* cited by examiner

*Primary Examiner* — Christina Bradley
(74) *Attorney, Agent, or Firm* — Foley & Lardner LLP

(57) ABSTRACT

This invention relates to: a peptide which comprises an amino acid sequence consisting of 12 to 18 amino acid residues represented by $(X_{1-3})-C-(X_{8-10})-C-(X_{1-3})$ wherein each X independently represents an arbitrary amino acid residue other than cysteine, and C represents a cysteine residue, and is capable of binding to human IgA; and to a method for analyzing or purifying human IgA using the peptide.

12 Claims, 14 Drawing Sheets

Fig. 3

| Position No. | 1 | 2 | 3 | 4 | 5 | 6 | 7 | 8 | 9 | 10 | 11 | 12 | 13 | 14 | 15 | 16 | |
|---|---|---|---|---|---|---|---|---|---|---|---|---|---|---|---|---|---|
| Amino acid | H | M | R | C | L | H | Y | K | G | R | R | V | C | F | L | L | (SEQ ID NO:1) |
| DNA | cat | atg | agg | tgt | ttg | cat | tac | aag | ggg | agg | agg | gtc | tgt | ttt | ttg | ttg | (SEQ ID NO:45) |

Fig. 10

| Position No. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Amino acid | X | X | X | C | L | X | Y | X | G | X | X | V | C | X | X | X |
| DNA | NNK | NNK | NNK | tgt | ttg | NNK | tac | NNK | ggg | NNK | NNK | gtc | tgt | NNK | NNK | NNK |

SEQUENCE LISTING

<160> NUMBER OF SEQ ID NOS: 46

<210> SEQ ID NO 1
<211> LENGTH: 16
<212> TYPE: PRT
<213> ORGANISM: Artificial
<220> FEATURE:
<223> OTHER INFORMATION: IgA-binding peptide

<400> SEQUENCE: 1

His Met Arg Cys Leu His Tyr Lys Gly Arg Arg Val Cys Phe Leu Leu
1               5                   10                  15

<210> SEQ ID NO 2
<211> LENGTH: 16
<212> TYPE: PRT
<213> ORGANISM: Artificial
<220> FEATURE:
<223> OTHER INFORMATION: IgA-binding peptide

<400> SEQUENCE: 2

Gln Met Arg Cys Leu Ser Tyr Lys Gly Arg Arg Val Cys Leu Trp Leu
1               5                   10                  15

<210> SEQ ID NO 3
<211> LENGTH: 16
<212> TYPE: PRT
<213> ORGANISM: Artificial
<220> FEATURE:
<223> OTHER INFORMATION: IgA-binding peptide

<400> SEQUENCE: 3

His Lys Arg Cys Leu His Tyr Arg Gly Arg Met Val Cys Phe Leu Ile
1               5                   10                  15

<210> SEQ ID NO 4
<211> LENGTH: 16
<212> TYPE: PRT
<213> ORGANISM: Artificial
<220> FEATURE:
<223> OTHER INFORMATION: IgA-binding peptide

<400> SEQUENCE: 4

Lys Arg Leu Cys Leu Gln Tyr Lys Gly Ser Lys Val Cys Phe Arg Leu
1               5                   10                  15

<210> SEQ ID NO 5
<211> LENGTH: 16
<212> TYPE: PRT
<213> ORGANISM: Artificial
<220> FEATURE:
<223> OTHER INFORMATION: IgA-binding peptide

<400> SEQUENCE: 5

Arg Met Arg Cys Leu Thr Tyr Arg Gly Arg Arg Val Cys Leu Glu Leu
1               5                   10                  15

<210> SEQ ID NO 6
<211> LENGTH: 16
<212> TYPE: PRT
<213> ORGANISM: Artificial
<220> FEATURE:
<223> OTHER INFORMATION: IgA-binding peptide

<400> SEQUENCE: 6

Ser Met Arg Cys Leu Gln Tyr Arg Gly Ser Arg Val Cys Leu Thr Leu
1               5                   10                  15

```
<210> SEQ ID NO 7
<211> LENGTH: 16
<212> TYPE: PRT
<213> ORGANISM: Artificial
<220> FEATURE:
<223> OTHER INFORMATION: IgA-binding peptide

<400> SEQUENCE: 7

Gln Lys Arg Cys Leu Lys Tyr Lys Gly Ser Arg Val Cys Phe Phe Leu
1               5                   10                  15

<210> SEQ ID NO 8
<211> LENGTH: 16
<212> TYPE: PRT
<213> ORGANISM: Artificial
<220> FEATURE:
<223> OTHER INFORMATION: IgA-binding peptide

<400> SEQUENCE: 8

His Leu Arg Cys Leu Arg Tyr Lys Gly Thr Arg Val Cys Phe Ser Leu
1               5                   10                  15

<210> SEQ ID NO 9
<211> LENGTH: 16
<212> TYPE: PRT
<213> ORGANISM: Artificial
<220> FEATURE:
<223> OTHER INFORMATION: IgA-binding peptide

<400> SEQUENCE: 9

His Val Arg Cys Leu Ser Tyr Lys Gly Arg Glu Val Cys Val Gln Leu
1               5                   10                  15

<210> SEQ ID NO 10
<211> LENGTH: 16
<212> TYPE: PRT
<213> ORGANISM: Artificial
<220> FEATURE:
<223> OTHER INFORMATION: IgA-binding peptide

<400> SEQUENCE: 10

Pro Arg Met Cys Leu His Tyr Lys Gly Arg Arg Val Cys Ile Pro Tyr
1               5                   10                  15

<210> SEQ ID NO 11
<211> LENGTH: 16
<212> TYPE: PRT
<213> ORGANISM: Artificial
<220> FEATURE:
<223> OTHER INFORMATION: IgA-binding peptide

<400> SEQUENCE: 11

His Val Arg Cys Leu Arg Tyr Arg Gly Lys Asn Val Cys Phe Leu Leu
1               5                   10                  15

<210> SEQ ID NO 12
<211> LENGTH: 17
<212> TYPE: PRT
<213> ORGANISM: Artificial
<220> FEATURE:
<223> OTHER INFORMATION: IgA-binding peptide

<400> SEQUENCE: 12

Ser Thr Phe Cys Leu Leu Gly Gln Lys Asp Gln Ser Tyr Cys Phe Thr
1               5                   10                  15
```

Ile

<210> SEQ ID NO 13
<211> LENGTH: 16
<212> TYPE: PRT
<213> ORGANISM: Artificial
<220> FEATURE:
<223> OTHER INFORMATION: IgA-binding peptide

<400> SEQUENCE: 13

Lys Thr Met Cys Leu Arg Tyr Asn His Asp Lys Val Cys Phe Arg Ile
1               5                   10                  15

<210> SEQ ID NO 14
<211> LENGTH: 18
<212> TYPE: PRT
<213> ORGANISM: Artificial
<220> FEATURE:
<223> OTHER INFORMATION: IgA-binding peptide

<400> SEQUENCE: 14

Leu Val Leu Cys Leu Val His Arg Thr Ser Lys His Arg Lys Cys Phe
1               5                   10                  15

Val Ile

<210> SEQ ID NO 15
<211> LENGTH: 16
<212> TYPE: PRT
<213> ORGANISM: Artificial
<220> FEATURE:
<223> OTHER INFORMATION: IgA-binding peptide

<400> SEQUENCE: 15

Ser Asp Val Cys Leu Arg Tyr Arg Gly Arg Pro Val Cys Phe Gln Val
1               5                   10                  15

<210> SEQ ID NO 16
<211> LENGTH: 16
<212> TYPE: PRT
<213> ORGANISM: Artificial
<220> FEATURE:
<223> OTHER INFORMATION: IgA-binding peptide

<400> SEQUENCE: 16

Arg Asp Val Cys Leu Arg Tyr Arg Gly Arg Pro Val Cys Phe Gln Val
1               5                   10                  15

<210> SEQ ID NO 17
<211> LENGTH: 16
<212> TYPE: PRT
<213> ORGANISM: Artificial
<220> FEATURE:
<223> OTHER INFORMATION: IgA-binding peptide

<400> SEQUENCE: 17

His Asp Val Cys Leu Arg Tyr Arg Gly Arg Pro Val Cys Phe Gln Val
1               5                   10                  15

<210> SEQ ID NO 18
<211> LENGTH: 16
<212> TYPE: PRT
<213> ORGANISM: Artificial
<220> FEATURE:
<223> OTHER INFORMATION: IgA-binding peptide

<400> SEQUENCE: 18

Ala Asp Val Cys Leu Arg Tyr Arg Gly Arg Pro Val Cys Phe Gln Val
1               5                   10                  15

<210> SEQ ID NO 19
<211> LENGTH: 16
<212> TYPE: PRT
<213> ORGANISM: Artificial
<220> FEATURE:
<223> OTHER INFORMATION: IgA-binding peptide

<400> SEQUENCE: 19

Ser Met Val Cys Leu Arg Tyr Arg Gly Arg Pro Val Cys Phe Gln Val
1               5                   10                  15

<210> SEQ ID NO 20
<211> LENGTH: 16
<212> TYPE: PRT
<213> ORGANISM: Artificial
<220> FEATURE:
<223> OTHER INFORMATION: IgA-binding peptide

<400> SEQUENCE: 20

Ser Ala Val Cys Leu Arg Tyr Arg Gly Arg Pro Val Cys Phe Gln Val
1               5                   10                  15

<210> SEQ ID NO 21
<211> LENGTH: 16
<212> TYPE: PRT
<213> ORGANISM: Artificial
<220> FEATURE:
<223> OTHER INFORMATION: IgA-binding peptide

<400> SEQUENCE: 21

Ser Asp Arg Cys Leu Arg Tyr Arg Gly Arg Pro Val Cys Phe Gln Val
1               5                   10                  15

<210> SEQ ID NO 22
<211> LENGTH: 16
<212> TYPE: PRT
<213> ORGANISM: Artificial
<220> FEATURE:
<223> OTHER INFORMATION: IgA-binding peptide

<400> SEQUENCE: 22

Ser Asp Ala Cys Leu Arg Tyr Arg Gly Arg Pro Val Cys Phe Gln Val
1               5                   10                  15

<210> SEQ ID NO 23
<211> LENGTH: 16
<212> TYPE: PRT
<213> ORGANISM: Artificial
<220> FEATURE:
<223> OTHER INFORMATION: IgA-binding peptide

<400> SEQUENCE: 23

Ser Asp Val Cys Ala Arg Tyr Arg Gly Arg Pro Val Cys Phe Gln Val
1               5                   10                  15

<210> SEQ ID NO 24
<211> LENGTH: 16
<212> TYPE: PRT
<213> ORGANISM: Artificial
<220> FEATURE:
<223> OTHER INFORMATION: IgA-binding peptide

<400> SEQUENCE: 24

Ser Asp Val Cys Leu Asn Tyr Arg Gly Arg Pro Val Cys Phe Gln Val
1               5                   10                  15

<210> SEQ ID NO 25
<211> LENGTH: 16
<212> TYPE: PRT
<213> ORGANISM: Artificial
<220> FEATURE:
<223> OTHER INFORMATION: IgA-binding peptide

<400> SEQUENCE: 25

Ser Asp Val Cys Leu His Tyr Arg Gly Arg Pro Val Cys Phe Gln Val
1               5                   10                  15

<210> SEQ ID NO 26
<211> LENGTH: 16
<212> TYPE: PRT
<213> ORGANISM: Artificial
<220> FEATURE:
<223> OTHER INFORMATION: IgA-binding peptide

<400> SEQUENCE: 26

Ser Asp Val Cys Leu Ala Tyr Arg Gly Arg Pro Val Cys Phe Gln Val
1               5                   10                  15

<210> SEQ ID NO 27
<211> LENGTH: 16
<212> TYPE: PRT
<213> ORGANISM: Artificial
<220> FEATURE:
<223> OTHER INFORMATION: IgA-binding peptide

<400> SEQUENCE: 27

Ser Asp Val Cys Leu Arg Ala Arg Gly Arg Pro Val Cys Phe Gln Val
1               5                   10                  15

<210> SEQ ID NO 28
<211> LENGTH: 16
<212> TYPE: PRT
<213> ORGANISM: Artificial
<220> FEATURE:
<223> OTHER INFORMATION: IgA-binding peptide

<400> SEQUENCE: 28

Ser Asp Val Cys Leu Arg Tyr Ala Gly Arg Pro Val Cys Phe Gln Val
1               5                   10                  15

<210> SEQ ID NO 29
<211> LENGTH: 16
<212> TYPE: PRT
<213> ORGANISM: Artificial
<220> FEATURE:
<223> OTHER INFORMATION: IgA-binding peptide

<400> SEQUENCE: 29

Ser Asp Val Cys Leu Arg Tyr Arg Ala Arg Pro Val Cys Phe Gln Val
1               5                   10                  15

<210> SEQ ID NO 30
<211> LENGTH: 16
<212> TYPE: PRT
<213> ORGANISM: Artificial
<220> FEATURE:
<223> OTHER INFORMATION: IgA-binding peptide

<400> SEQUENCE: 30

Ser Asp Val Cys Leu Arg Tyr Arg Gly Ser Pro Val Cys Phe Gln Val
1               5                   10                  15

<210> SEQ ID NO 31
<211> LENGTH: 16
<212> TYPE: PRT
<213> ORGANISM: Artificial
<220> FEATURE:
<223> OTHER INFORMATION: IgA-binding peptide

<400> SEQUENCE: 31

Ser Asp Val Cys Leu Arg Tyr Arg Gly Ala Pro Val Cys Phe Gln Val
1               5                   10                  15

<210> SEQ ID NO 32
<211> LENGTH: 16
<212> TYPE: PRT
<213> ORGANISM: Artificial
<220> FEATURE:
<223> OTHER INFORMATION: IgA-binding peptide

<400> SEQUENCE: 32

Ser Asp Val Cys Leu Arg Tyr Arg Gly Arg Arg Val Cys Phe Gln Val
1               5                   10                  15

<210> SEQ ID NO 33
<211> LENGTH: 16
<212> TYPE: PRT
<213> ORGANISM: Artificial
<220> FEATURE:
<223> OTHER INFORMATION: IgA-binding peptide

<400> SEQUENCE: 33

Ser Asp Val Cys Leu Arg Tyr Arg Gly Arg Ala Val Cys Phe Gln Val
1               5                   10                  15

<210> SEQ ID NO 34
<211> LENGTH: 16
<212> TYPE: PRT
<213> ORGANISM: Artificial
<220> FEATURE:
<223> OTHER INFORMATION: IgA-binding peptide

<400> SEQUENCE: 34

Ser Asp Val Cys Leu Arg Tyr Arg Gly Arg Pro Ala Cys Phe Gln Val
1               5                   10                  15

<210> SEQ ID NO 35
<211> LENGTH: 16
<212> TYPE: PRT
<213> ORGANISM: Artificial
<220> FEATURE:
<223> OTHER INFORMATION: IgA-binding peptide

<400> SEQUENCE: 35

Ser Asp Val Cys Leu Arg Tyr Arg Gly Arg Pro Val Cys Arg Gln Val
1               5                   10                  15

<210> SEQ ID NO 36
<211> LENGTH: 16
<212> TYPE: PRT
<213> ORGANISM: Artificial
<220> FEATURE:
<223> OTHER INFORMATION: IgA-binding peptide

<400> SEQUENCE: 36

Ser Asp Val Cys Leu Arg Tyr Arg Gly Arg Pro Val Cys Ala Gln Val
1               5                   10                  15

<210> SEQ ID NO 37
<211> LENGTH: 16
<212> TYPE: PRT
<213> ORGANISM: Artificial
<220> FEATURE:
<223> OTHER INFORMATION: IgA-binding peptide

<400> SEQUENCE: 37

Ser Asp Val Cys Leu Arg Tyr Arg Gly Arg Pro Val Cys Phe Arg Val
1               5                   10                  15

<210> SEQ ID NO 38
<211> LENGTH: 16
<212> TYPE: PRT
<213> ORGANISM: Artificial
<220> FEATURE:
<223> OTHER INFORMATION: IgA-binding peptide

<400> SEQUENCE: 38

Ser Asp Val Cys Leu Arg Tyr Arg Gly Arg Pro Val Cys Phe Leu Val
1               5                   10                  15

<210> SEQ ID NO 39
<211> LENGTH: 16
<212> TYPE: PRT
<213> ORGANISM: Artificial
<220> FEATURE:
<223> OTHER INFORMATION: IgA-binding peptide

<400> SEQUENCE: 39

Ser Asp Val Cys Leu Arg Tyr Arg Gly Arg Pro Val Cys Phe Ala Val
1               5                   10                  15

<210> SEQ ID NO 40
<211> LENGTH: 16
<212> TYPE: PRT
<213> ORGANISM: Artificial
<220> FEATURE:
<223> OTHER INFORMATION: IgA-binding peptide

<400> SEQUENCE: 40

Ser Asp Val Cys Leu Arg Tyr Arg Gly Arg Pro Val Cys Phe Gln Trp
1               5                   10                  15

<210> SEQ ID NO 41
<211> LENGTH: 16
<212> TYPE: PRT
<213> ORGANISM: Artificial
<220> FEATURE:
<223> OTHER INFORMATION: IgA-binding peptide

<400> SEQUENCE: 41

Ser Asp Val Cys Leu Arg Tyr Arg Gly Arg Pro Val Cys Phe Gln Leu
1               5                   10                  15

<210> SEQ ID NO 42
<211> LENGTH: 16
<212> TYPE: PRT
<213> ORGANISM: Artificial
<220> FEATURE:
<223> OTHER INFORMATION: IgA-binding peptide

<400> SEQUENCE: 42

Ser Asp Val Cys Leu Arg Tyr Arg Gly Arg Pro Val Cys Phe Gln Ala
1               5                   10                  15

```
<210> SEQ ID NO 43
<211> LENGTH: 16
<212> TYPE: PRT
<213> ORGANISM: Artificial
<220> FEATURE:
<223> OTHER INFORMATION: IgA-binding peptide

<400> SEQUENCE: 43

His Met Val Cys Leu Ala Tyr Arg Gly Arg Pro Val Cys Phe Ala Leu
1               5                   10                  15

<210> SEQ ID NO 44
<211> LENGTH: 16
<212> TYPE: PRT
<213> ORGANISM: Artificial
<220> FEATURE:
<223> OTHER INFORMATION: IgA-binding peptide

<400> SEQUENCE: 44

His Met Val Cys Leu Ser Tyr Arg Gly Arg Pro Val Cys Phe Ser Leu
1               5                   10                  15

<210> SEQ ID NO 45
<211> LENGTH: 48
<212> TYPE: DNA
<213> ORGANISM: Artificial
<220> FEATURE:
<223> OTHER INFORMATION: DNA encoding IgA-binding peptide A-2

<400> SEQUENCE: 45
catatgaggt gtttgcatta caaggggagg agggtctgtt ttttgttg              48

<210> SEQ ID NO 46
<211> LENGTH: 16
<212> TYPE: PRT
<213> ORGANISM: Artificial
<220> FEATURE:
<223> OTHER INFORMATION: IgA-binding peptide
<220> FEATURE:
<221> NAME/KEY: misc_feature
<222> LOCATION: (1)..(1)
<223> OTHER INFORMATION: Xaa is Gln, His, Lys, Arg, Ser, or Pro
<220> FEATURE:
<221> NAME/KEY: misc_feature
<222> LOCATION: (2)..(2)
<223> OTHER INFORMATION: Xaa is Met, Lys, Arg, Leu, or Val
<220> FEATURE:
<221> NAME/KEY: misc_feature
<222> LOCATION: (3)..(3)
<223> OTHER INFORMATION: Xaa is Arg, Leu, or Met
<220> FEATURE:
<221> NAME/KEY: misc_feature
<222> LOCATION: (6)..(6)
<223> OTHER INFORMATION: Xaa is Ser, His, Gln, Thr, Lys, or Arg
<220> FEATURE:
<221> NAME/KEY: misc_feature
<222> LOCATION: (8)..(8)
<223> OTHER INFORMATION: Xaa is Lys or Arg
<220> FEATURE:
<221> NAME/KEY: misc_feature
<222> LOCATION: (10)..(10)
<223> OTHER INFORMATION: Xaa is Arg, Ser, Thr, or Lys
<220> FEATURE:
<221> NAME/KEY: misc_feature
<222> LOCATION: (11)..(11)
<223> OTHER INFORMATION: Xaa is Arg, Met, Lys, Glu, or Asn
<220> FEATURE:
<221> NAME/KEY: misc_feature
<222> LOCATION: (14)..(14)
<223> OTHER INFORMATION: Xaa is Leu, Phe, Val, or Ile
<220> FEATURE:
<221> NAME/KEY: misc_feature
<222> LOCATION: (15)..(15)
```

```
<223> OTHER INFORMATION: Xaa is Trp, Leu, Arg, Glu, Thr, Ser, Gln, or
      Pro
<220> FEATURE:
<221> NAME/KEY: misc_feature
<222> LOCATION: (16)..(16)
<223> OTHER INFORMATION: Xaa is Leu, Ile, or Tyr

<400> SEQUENCE: 46

Xaa Xaa Xaa Cys Leu Xaa Tyr Xaa Gly Xaa Xaa Val Cys Xaa Xaa Xaa
1               5                   10                  15
```

IGA-BINDING PEPTIDE AND PURIFICATION OF IGA USING THE SAME

CROSS-REFERENCE TO RELATED APPLICATIONS

This application is a national phase of PCT/JP2011/061906, filed May 24, 2011, which was published on Dec. 1, 2011, as WO 2011/148952, and which claims the benefit of JP Appln No. 2010-118508, filed May 24, 2010. The respective contents of these applications are incorporated herein by reference in their entirety.

The instant application contains a Sequence Listing which has been submitted in ASCII format via EFS-WEB and is hereby incorporated by reference in its entirety. Said ASCII copy, created on Mar. 14, 2016, is named sequence.txt and is 12 KB.

TECHNICAL FIELD

The present invention relates to a human IgA-binding peptide obtained from a random peptide library, and to a method for analyzing or purifying IgA using the peptide.

BACKGROUND ART

Immunoglobulin A (IgA) is not only an important antibody for mucosal immunity but also constitutes the second major antibody class following immunoglobulin G (IgG) in blood and works to defend against bacterial or viral infections. IgA includes secretory IgA (sIgA) having a dimeric structure and IgA having a monomeric structure (mIgA). sIgA has a dimeric structure in which the monomeric units are linked by a joining chain (J-chain) through disulfide bonds, and is secreted into mucus, while mIgA is mostly found in blood. Also, IgA has two subtypes: IgA1 and IgA2, which differ mainly in the length of the hinge region. IgA2 is deficient in a Pro-rich region of 13 residues. The functions of IgA directed to pharmaceuticals have been focused on the development of mucosal vaccines because of its importance for immunity against infections (Non-Patent Literatures 1 and 2). IgA in blood has been reported to have ADCC against cancer cells particularly mediated by neutrophils (Non-Patent Literatures 3 and 4). IgA can thus be expected as a cancer-targeting antibody drug, as in IgG, which is an antibody drug format whose clinical application is being expanded as a therapeutic drug for cancer or autoimmune disease (Non-Patent Literature 5).

However, there are some impediments to the pharmaceutical development of IgA, including the absence of a purification method that can work on an industrial or pharmaceutical scale as in protein A/G affinity columns for IgG production. Some methods have previously been reported as methods for purifying IgA (Non-Patent Literature 6). The reported methods for purifying IgA utilize, for example, Jackalin, a lectin recognizing an IgA1-specific sugar chain (Non-Patent Literature 7) or a protein A-mimetic synthetic ligand TG19318 (Non-Patent Literature 8). These methods are limited in use due to problems associated with binding ability or specificity. IgA-binding proteins have been found from members of the family of NI proteins (Non-Patent Literature 9), surface proteins derived from *Streptococcus* bacteria (Non-Patent Literatures 10 and 11 and Patent Literature 1). These IgA-binding proteins, however, have, for example, unfavorable interactions with other proteins in serum, such as IgG (Non-Patent Literature 12) and have failed to be used as IgA-specific affinity ligands. Meanwhile, Sandin et al. reported that they isolated a domain peptide (Streptococcal IgA-binding peptide, Sap) consisting of 48 residues in the Streptococcal Sir22 (M22) protein and formed a disulfide-bonded dimer thereof via Cys to obtain an affinity ligand for IgA purification having relatively high affinity (Kd: 20 nM), albeit lower than the affinity of the original Sir22 protein (Kd: 3 to 4 nM; Non-Patent Literature 13 and Patent Literature 2). In actuality, this ligand was capable of binding to IgA Fc and was also applicable to the purification of both sIgA and mIgA and the detection of antigen-specific IgA1 and IgA2 monoclonal antibodies.

Also, for IgG, IgG-binding peptides have been developed by the present inventors (Patent Literature 3), as in the IgA-binding proteins.

PRIOR ART LITERATURE

Patent Literature

Patent Literature 1: International Publication No. WO 1992/017588
Patent Literature 2: International Publication No. WO 2000/063383
Patent Literature 3: International Publication No. WO 2008/054030

Non-Patent Literature

Non-Patent Literature 1: Holmgren, J. (1991) Fems Microbiology Immunology 89 (1), 1-9
Non-Patent Literature 2: Holmgren, J., and Czerkinsky, C. (2005) Nat. Med. 11 (4), S45-S53
Non-Patent Literature 3: Dechant, M., Beyer, T., Schneider-Merck, T., Weisner, W., Peipp, M., van de Winkel, J. G., and Valcrius, T. (2007) J Immunol 179 (5), 2936-2943
Non-Patent Literature 4: Zhao, J., Kuroki, M., Shibaguchi, H., Wang, L., Huo, Q., Takami, N., Tanaka, T., Kinugasa, T., and Kuroki, M. (2008) Oncol. Res. 17 (5), 217-222
Non-Patent Literature 5: Beyer, T., Lohse, S., Berger, S., Peipp, M., Valerius, T., and Dechant, M. (2009) Journal of Immunological Methods 346 (1-2), 26-37
Non-Patent Literature 6: Pack, T. D. (2001) Current protocols in Immunology/edited by John E. Coligan et al., Chapter 2. Unit 2 10B
Non-Patent Literature 7: Kondoh, H., Kobayashi, K., and Hagiwara, K. (1987) Molecular immunology 24 (11), 1219-1222
Non-Patent Literature 8: Palombo, G., De Falco, S., Tortora, M., Cassani, G., and Fassina, G. (1998) J Mol Recognit 11 (1-6), 243-246
Non-Patent Literature 9: Frithz, E., Heden, L. O., and Lindahl, G. (1989) Molecular Microbiology 3 (8), 1111-1119
Non-Patent Literature 10: Russell-Jones, G. J., Gotschlich, E. C., and Blake, M. S. (1984) The Journal of Experimental Medicine 160 (5), 1467-1475
Non-Patent Literature 11: Lindahl, G., Akerstrom, B., Vaerman, J. P., and Stenberg, L. (1990) European Journal of Immunology 20 (10), 2241-2247
Non-Patent Literature 12: Stenberg, L., O'Toole, P. W., Mestecky, J., and Lindahl, G. (1994) The Journal of Biological Chemistry 269 (18), 13458-13464
Non-Patent Literature 13: Sandin, C., Linse, S., Areschoug, T., Woof, J. M., Reinholdt, J., and Lindahl, G. (2002) J Immunol 169 (3), 1357-1364

SUMMARY OF INVENTION

Problem to be Solved by the Invention

An object of the present invention is to provide a peptide capable of specifically or selectively binding to human IgA.

Another object of the present invention is to provide a method for purifying or analyzing (e.g., detecting or quantifying) human IgA using the peptide.

Means for Solving the Problem

As described in Background Art, human IgA is present in mucosa and blood and plays an important role in defending against infections, etc. Because of such properties, IgA is to be used as an antibody drug in the treatment of disease such as infectious disease or tumor. In consideration of such circumstances, the present invention provides a peptide capable of specifically or selectively binding to human IgA and is thereby considered useful for the purification and analysis of IgA that can be used pharmaceutically.

In short, the present invention has the following aspects:

[1] A peptide which comprises an amino acid sequence consisting of 12 to 18 amino acid residues represented by the following formula I and is capable of binding to human IgA:

$$(X_{1-3})-C-(X_{8-10})-C-(X_{1-3}) \quad (I)$$

wherein each X independently represents an arbitrary amino acid residue other than cysteine; and C represents a cysteine residue.

[2] The peptide according to [1], wherein the peptide comprises an amino acid sequence consisting of 16 to 18 amino acid residues represented by the following formula II and is capable of binding to human IgA:

$$(X_3)-C-L-(X_{7-9})-C-(X_3) \quad (II)$$

wherein each X independently represents an arbitrary amino acid residue other than cysteine; C represents a cysteine residue; and L represents a leucine residue, and wherein the 9th and 10th amino acid residues Xs counted from the N terminus in the case that the number of amino acid residues of the peptide is regarded as 18 amino acid residues, each independently represent an arbitrary amino acid residue other than cysteine, or either of the 9th and 10th amino acid residues Xs, or both, are deleted.

[3] The peptide according to [2], wherein the peptide comprises an amino acid sequence consisting of 16 to 18 amino acid residues represented by the following formula III and is capable of binding to human IgA:

$$(X_3)-C-L-X-Y-(X_{1-3})-G-(X_2)-V-C-(X_3) \quad (III)$$

wherein each X independently represents an arbitrary amino acid residue other than cysteine; C represents a cysteine residue; L represents a leucine residue; Y represents a tyrosine residue; G represents a glycine residue; and V represents a valine residue, and wherein the 9th and 10th amino acid residues Xs counted from the N terminus in the case that the number of amino acid residues of the peptide is regarded as 18 amino acid residues, each independently represent an arbitrary amino acid residue other than cysteine, or either of the 9th and 10th amino acid residue Xss, or both, are deleted.

[4] The peptide according to [3], wherein the peptide comprises an amino acid sequence consisting of 16 to 18 amino acid residues represented by the following formula IV and is capable of binding to human IgA:

$$(X_3)-C-L-X-Y-(X_{1-3})-O-(X_2)-V-C-(X_3) \quad (IV)$$

wherein each X independently represents an arbitrary amino acid residue other than cysteine; C represents a cysteine residue; L represents a leucine residue; Y represents a tyrosine residue; G represents a glycine residue; and V represents a valine residue, and wherein the 9th and 10th amino acid residues Xs counted from the N terminus in the case that the number of amino acid residues of the peptide is regarded as 18 amino acid residues, each independently represent an arbitrary amino acid residue other than cysteine, or either of the 9th and 10th amino acid residues Xs, or both, are deleted, and the 16th and 18th amino acid residues counted from the N terminus each independently represent a hydrophobic amino acid residue.

[5] The peptide according to any of [1] to [4], wherein the 1st to 3rd, 5th to 14th, and 16th to 18th amino acid residues counted from the N terminus in the case that the number of amino acid residues of the peptide is regarded as 18 amino acid residues, are respectively 1st amino acid residue=Q, H, K, R, S, or P,
2nd amino acid residue=M, K, R, L, V, A, or D,
3rd amino acid residue=R, L, M, or V,
5th amino acid residue=L,
6th amino acid residue S, H, Q, T, K, R, N, or A,
7th amino acid residue=Y,
8th amino acid residue=K or R,
9th amino acid residue=an arbitrary amino acid residue other than C or deleted,
10th amino acid residue=an arbitrary amino acid residue other than C or deleted,
11th amino acid residue=G,
12th amino acid residue=R, S, T, or K,
13th amino acid residue=R, M, K, E, N, or P,
14th amino acid residue=V,
16th amino acid residue=L, F, V, or I,
17th amino acid residue=W, L, R, E, T, S, Q, P, or A, and
18th amino acid residue=L, I, Y, A, or V.

[6] The peptide according to any of [1] to [5], wherein the 16th amino acid residue X counted from the N terminus in the case that the number of amino acid residues of the peptide is regarded as 18 amino acid residues in any of the peptides of the formulas I to IV is a leucine or phenylalanine residue.

[7] The peptide according to any of [1] to [6], wherein the 18th amino acid residue X counted from the N terminus in the case that the number of amino acid residues of the peptide is regarded as 18 amino acid residues in any of the peptides of the formulas I to IV is a leucine residue.

[8] the peptide according to any of [1] to [7], wherein the peptide consists of any of the following amino acid sequences 1) to 26):

| | | |
|---|---|---|
| 1) | HMRCLHYKGRRVCFLL, | (SEQ ID NO: 1) |
| 2) | QMRCLSYKGRRVCLWL, | (SEQ ID NO: 2) |
| 3) | HKRCLHYRGRMVCFLI, | (SEQ ID NO: 3) |
| 4) | KRLCLQYKGSKVCFRL, | (SEQ ID NO: 4) |
| 5) | RMRCLTYRGRRVCLEL, | (SEQ ID NO: 5) |
| 6) | SMRCLQYRGSRVCLTL, | (SEQ ID NO: 6) |
| 7) | QKRCLKYKGSRVCFFL, | (SEQ ID NO: 7) |
| 8) | HLRCLRYKGTRVCFSL, | (SEQ ID NO: 8) |
| 9) | HVRCLSYKGREVCVQL, | (SEQ ID NO: 9) |

-continued

| | | |
|---|---|---|
| 10) | PRMCLHYKGRRVCIPY, | (SEQ ID NO: 10) |
| 11) | HVRCLRYRGKNVCFLL, | (SEQ ID NO: 11) |
| 12) | SDVCLRYRGRPVCFQV, | (SEQ ID NO: 15) |
| 13) | RDVCLRYRGRPVCFQV, | (SEQ ID NO: 16) |
| 14) | HDVCLRYRGRPVCFQV, | (SEQ ID NO: 17) |
| 15) | SMVCLRYRGRPVCFQV, | (SEQ ID NO: 19) |
| 16) | SAVCLRYRGRPVCFQV, | (SEQ ID NO: 20) |
| 17) | SDVCLNYRGRPVCFQV, | (SEQ ID NO: 24) |
| 18) | SDVCLHYRGRPVCFQV, | (SEQ ID NO: 25) |
| 19) | SDVCLAYRGRPVCFQV, | (SEQ ID NO: 26) |
| 20) | SDVCLRYRGRPVCFRV, | (SEQ ID NO: 37) |
| 21) | SDVCLRYRGRPVCFLV, | (SEQ ID NO: 38) |
| 22) | SDVCLRYRGRPVCFAV, | (SEQ ID NO: 39) |
| 23) | SDVCLRYRGRPVCFQL, | (SEQ ID NO: 41) |
| 24) | SDVCLRYRGRPVCFQA, | (SEQ ID NO: 42) |
| 25) and | HMVCLAYRGRPVCFAL, | (SEQ ID NO: 43) |
| 26) | HMVCLSYRGRPVCFSL. | (SEQ ID NO: 44) |

[9] The peptide according to any of [1] to [8], wherein the peptide has a disulfide bond between its two cysteine (C) residues.

[10] The peptide according to any of [1] to [9], wherein the peptide binds to serum (monomeric) IgA and secretory (dimeric) IgA.

[11] The peptide according to any of [1] to [10], wherein the peptide is labeled.

[12] A fusion protein comprising a protein linked to a peptide according to any of [1] to [11].

[13] An immobilized peptide comprising a peptide according to any of [1] to [11] bound with a solid phase.

[14] A nucleic acid encoding a peptide according to any of [1] to [11].

[15] A method for purifying IgA, comprising: binding a peptide according to any of [1] to [11] or an immobilized peptide according [13] to IgA; and releasing bound IgA to collect the IgA.

[16] A method for detecting IgA, comprising binding a peptide according to any of [1] to [11] or an immobilized peptide according to [13] to IgA in a sample and detecting bound IgA.

[17] A kit for analysis or purification of human IgA, comprising at least one peptide according to any one of [1] to [11] or immobilized peptide according to [13].

[18] A column for IgA separation. comprising an immobilized peptide according to [13].

The present specification incorporates the contents described in the specification and/or drawings of Japanese Patent Application No. 2010-118508, from which the present application claims the priority.

The human IgA-binding peptide of the present invention is advantageously capable of binding to human IgA with high selectivity, compared with IgG, IgM, and IgE. This means that use of this peptide allows selective separation of IgA from, for example, human serum, or the like.

BRIEF DESCRIPTION OF DRAWINGS

FIG. 3 shows the amino acid sequence and DNA sequence of an hIgA-2 peptide motif.

FIG. 10 shows the design of an optimized library for isolating a motif having high affinity for hIgA.

MODE FOR CARRYING OUT THE INVENTION

Figure 1:
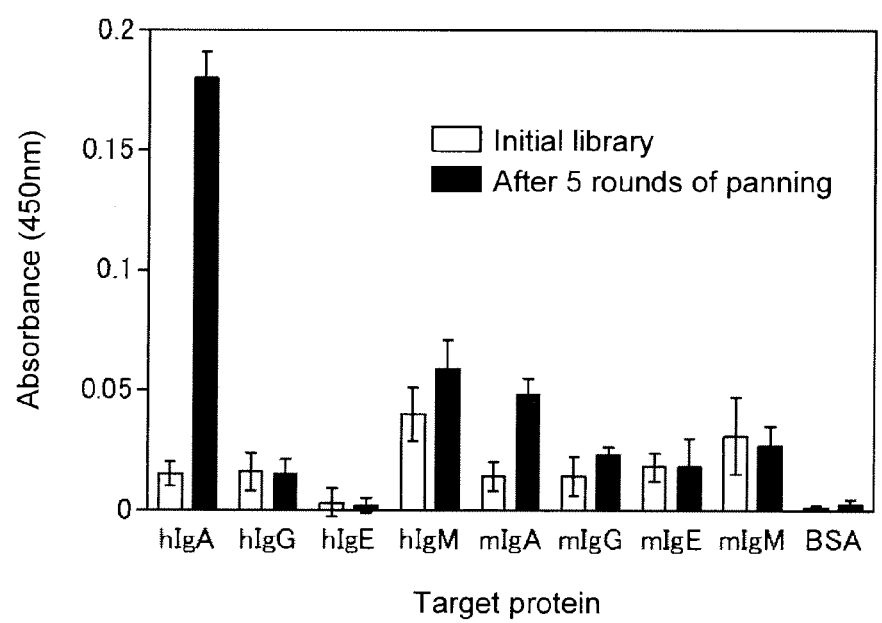
FIG. 1 shows the binding specificity, measured by ELISA, of a phage obtained after 5 rounds of panning for human IgA.

The peptides capable of specifically or selectively binding to human IgA, which were found by the present inventors this time, were isolated by a biopanning method from a library newly designed and constructed with reference to a random peptide library (Sakamoto, K., Ito, Y., Hatanaka, T., Soni, P. B., Mori, T., and Sugimura, K. (2009) The Journal of Biological Chemistry 284 (15), 9986-9993) involving peptides each containing one intramolecular disulfide bond constructed with the T7 phage display system. Four specific clones obtained by this method exhibited sequence homology common to each other. Synthetic peptides prepared by various substitutions or deletions on the basis of their sequences exhibited excellent specificity and affinity for IgA. Residues essential for the IgA binding of these peptides were identified to achieve an approach to enhanced affinity and an application to purification of IgA from human serum using the peptides. The most compact, i.e., smallest molecules of the IgA-binding peptides of the present invention each consist of 12 or 13 residues and are as small as about ¼ in size of the *Streptococcus* Sir22 (M22)-derived Sap peptide of approximately 50 residues (having one Cys residue at the C-terminal end) described in Non-Patent Literature 13. As a result, the construction of an IgA purification system based on these peptides can be expected at low cost.

Hereinafter, the present invention will be described in more detail.

Specifically, each IgA-binding peptide of the present invention, a method for purifying or analyzing IgA using the peptide, a kit for such IgA purification or detection will be described.

(IgA-Binding Peptide)

The peptides of the present invention were obtained by screening a phage library containing a large number of random peptides for specific or selective binding to human IgA. The peptides of the present invention differ in their origins and primary structures from conventional polypeptides known in the art as described in Non-Patent Literature 13.

The human IgA used in the present specification refers to IgA1 and/or IgA2.

Specifically, the peptide of the present invention comprises an amino acid sequence consisting of 12 to 18 amino acid residues represented by the following formula I in terms of the primary structure in the broadest sense and is capable of binding to human IgA:

$$(X_{1-3})-C-(X_{8-10})-C-(X_{1-3}) \qquad (I)$$

wherein each X independently represents an arbitrary amino acid residue other than cysteine; and C represents a cysteine residue.

In the above formula, the term $X_{1-3}$ at the N or C terminus means 1 to 3 consecutive amino acid residues X arbitrarily and independently selected from residues other than cysteine (C or Cys). The amino acid residues constituting this moiety are the same as or different from each other. Preferably, this sequence consists of residues, three of which are all different from each other. Likewise, $X_{8-10}$ also means 8 to 10 consecutive amino acid residues X arbitrarily and independently selected from residues other than cysteine (C or Cys). The amino acid residues constituting this moiety are the same as or different from each other. Preferably, this sequence consists of residues, three or more of which are different from each other. The same meaning is applied to the terms $X_3$, $X_{7-9}$, $X_2$, etc., in formulas shown below.

Two cysteine residues in the formula I can be disulfide-bonded to form a cyclic peptide. Typically, the peptide of the formula I has this disulfide bond.

Peptides derived from the peptide of the formula I as having further defined amino acid residues Xs in their amino acid sequences are represented by the formulas II, III, and IV and shown below.

Specifically, a peptide represented by the formula II:

$$(X_3)-C-L-(X_{7-9})-C-(X_3) \qquad (II)$$

wherein each X independently represents an arbitrary amino acid residue other than cysteine; C represents a cysteine residue; and L represents a leucine residue, and wherein the 9th and 10th amino acid residues X counted from the N terminus in the case that the number of amino acid residues of the peptide is regarded as 18 amino acid residues, each independently represent an arbitrary amino acid residue other than cysteine, or either of the 9th and 10th amino acid residues, or both, are deleted,
comprises this amino acid sequence consisting of 16 to 18 amino acid residues and is capable of binding to human IgA.

A peptide represented by the formula III:

$$(X_3)-C-L-X-Y-(X_{1-3})-G-(X_2)-V-C-(X_3) \qquad (III)$$

wherein each X independently represents an arbitrary amino acid residue other than cysteine; C represents a cysteine residue; L represents a leucine residue; Y represents a tyrosine residue; G represents a glycine residue; and V represents a valine residue, and wherein the 9th and 10th amino acid residues X counted from the N terminus in the case that the number of amino acid residues of the peptide is regarded as 18 amino acid residues, each independently represent an arbitrary amino acid residue other than cysteine, or either of the 9th and 10th amino acid residues, or both, are deleted,
comprises this amino acid sequence consisting of 16 to 18 amino acid residues and is capable of binding to human IgA.

A peptide represented by the formula IV:

$$(X_3)-C-L-X-Y-(X_{1-3})-G-(X_2)-V-C-(X_3) \qquad (IV)$$

wherein each X independently represents an arbitrary amino acid residue other than cysteine; C represents a cysteine residue; L represents a leucine residue; Y represents a tyrosine residue; G represents a glycine residue; and V represents a valine residue, and wherein the 9th and 10th amino acid residues X counted from the N terminus in the case that the number of amino acid residues of the peptide is regarded as 18 amino acid residues, each independently represent an arbitrary amino acid residue other than cysteine, or either of the 9th and 10th amino acid residues, or both, are deleted, and the 16th and 18th amino acid residues counted from the N terminus each independently represent a hydrophobic amino acid residue,
comprises this amino acid sequence consisting of 16 to 18 amino acid residues and is capable of binding to human IgA.

Preferably, both the 9th and 10th amino acid residues Xs counted from the N terminus are deleted in the case that the number of amino acid residues of the peptide is regarded as 18 amino acid residues in each of the amino acid sequences of the peptides of the formulas II to IV. Such a peptide is 16 amino acids long.

The phrase "in the case that the number of amino acid residues of the peptide is regarded as 18 amino acid residues" as used herein is used for the sake of convenience to number 18 residues (the largest amino acid length) 1 through 18 in order from the N terminus when the amino acid residues in the peptide are designated according to the numbers of amino acid positions.

Preferably, the amino acid residues other than cysteine (C) in the amino acid sequence of the peptide of each formula, i.e., the 1st to 3rd, 5th to 14th, and 16th to 18th amino acid residues counted from the N terminus in the case that the number of amino acid residues of the peptide is regarded as 18 amino acid residues, are respectively selected from the followings (where each capital alphabet represents a single-letter amino acid):

1st amino acid residue=Q, H, K, R, S, or P, preferably H,
2nd amino acid residue=M, K, R, L, V, A. or D, preferably M,
3rd amino acid residue=R, L, M, or V, preferably V,
5th amino acid residue=L,
6th amino acid residue=S, H, Q, T, K, R, N, or A, preferably S or A,
7th amino acid residue=Y,
8th amino acid residue=K or R, preferably R,
9th amino acid residue=an arbitrary amino acid residue other than C or deleted, preferably, deleted,
10th amino acid residue=an arbitrary amino acid residue other than C or deleted, preferably, deleted,
11th amino acid residue=G,
12th amino acid residue=R, S, T, or K, preferably R,
13th amino acid residue=R, M, K, E, N, or P, preferably P,
14th amino acid residue=V,
16th amino acid residue=L, F, V, or I, preferably L or F, 17th amino acid residue=W, L, R, E, T, S, Q, P, or A, preferably S or A, and 18th amino acid residue=L, I, Y, A, or V, preferably L.

Some specific examples of the peptides of the present invention will be listed in 1) to 26) below. As a matter of course, the peptides of the present invention are not limited to these examples. All of such peptides have much higher binding specificity or binding selectivity for human IgA than those for immunoglobulins of other species.

| | | |
|---|---|---|
| 1) | HMRCLHYKGRRVCFLL | (SEQ ID NO: 1) |
| 2) | QMRCLSYKGRRVCLWL | (SEQ ID NO: 2) |
| 3) | HKRCLHYRGRMVCFLI | (SEQ ID NO: 3) |
| 4) | KRLCLQYKGSKVCFRL | (SEQ ID NO: 4) |
| 5) | RMRCLTYRGRRVCLEL | (SEQ ID NO: 5) |
| 6) | SMRCLQYRGSRVCLTL | (SEQ ID NO: 6) |
| 7) | QKRCLKYKGSRVCFFL | (SEQ ID NO: 7) |
| 8) | HLRCLRYKGTRVCFSL | (SEQ ID NO: 8) |
| 9) | HVRCLSYKGREVCVQL | (SEQ ID NO: 9) |
| 10) | PRMCLHYKGRRVCIPY | (SEQ ID NO: 10) |
| 11) | HVRCLRYRGKNVCFLL | (SEQ ID NO: 11) |
| 12) | SDVCLRYRGRPVCFQV | (SEQ ID NO: 15) |
| 13) | RDVCLRYRGRPVCFQV | (SEQ ID NO: 16) |
| 14) | HDVCLRYRGRPVCFQV | (SEQ ID NO: 17) |
| 15) | SMVCLRYRGRPVCFQV | (SEQ ID NO: 19) |
| 16) | SAVCLRYRGRPVCFQV | (SEQ ID NO: 20) |
| 17) | SDVCLNYRGRPVCFQV | (SEQ ID NO: 24) |
| 18) | SDVCLHYRGRPVCFQV | (SEQ ID NO: 25) |
| 19) | SDVCLAYRGRPVCFQV | (SEQ ID NO: 26) |
| 20) | SDVCLRYRGRPVCFRV | (SEQ ID NO: 37) |
| 21) | SDVCLRYRGRPVCFLV | (SEQ ID NO: 38) |
| 22) | SDVCLRYRGRPVCFAV | (SEQ ID NO: 39) |
| 23) | SDVCLRYRGRPVCFQL | (SEQ ID NO: 41) |
| 24) | SDVCLRYRGRPVCFQA | (SEQ ID NO: 42) |
| 25) | HMVCLAYRGRPVCFAL | (SEQ ID NO: 43) |
| 26) | HMVCLSYRGRPVCFSL | (SEQ ID NO: 44) |

Of these 26 peptides, particularly, the peptides of SEQ ID NO: 43 (A3-1(Opt1)) and SEQ ID NO: 44 (A3-1(Opt2)) have higher affinity for human IgA (also referred to as "hIgA").

As described above, each of the peptides of the formulas according to the present invention has two discrete cysteine (C) residues in its amino acid sequence. The peptides are characterized in that these cysteine residues are arranged so as to form a disulfide bond between the cysteine residues. A preferable peptide is a cyclic peptide formed through the disulfide bond between these two cysteine residues, wherein 1 to 3, preferably 3 arbitrary amino acid residues other than cysteine are positioned on the N-terminal or C-terminal side of each cysteine residue. The 1st to 3rd and 16th to 18th amino acid residues are as exemplified above.

The peptides of the present invention have binding affinity for human IgA at least about 10 times, preferably at least about 50 times, more preferably at least about 200 times higher than that for other human immunoglobulins (IgG, IgE, and IgM). The dissociation constant (Kd) in the binding of the peptides of the present invention with human IgA can be determined by surface plasmon resonance spectrum analysis (using. e.g., BIACORE system (protein interaction analysis)) and is, for example, $1 \times 10^{-5}$ M to less than $1 \times 10^{-7}$ M, preferably less than $1 \times 10^{-8}$ M, more preferably less than $1 \times 10^{-9}$ M, further preferably less than $1 \times 10^{-10}$ M.

A peptide of the present invention immobilized on a solid phase was actually used in a test on binding to IgA in human serum and consequently found to bind to serum (monomeric) IgA and secretory (dimeric) IgA, showing that separation of either form of IgA is possible.

A peptide of the present invention can be produced by, for example, a peptide synthesis method routinely used, such as a liquid-phase or solid-phase synthesis method, or peptide synthesis using an automatic peptide synthesizer (Kelley et al., Genetics Engineering Principles and Methods, Setlow, J. K. eds., Plenum Press NY. (1990) Vol. 12, p. 1-19; S tewart et al., Solid-Phase Peptide Synthesis (1989) W.H. Freeman Co.; Houghten, Proc. Natl. Acad. Sci. USA (1985) 82: p. 5132; and "Shin Seikagaku Jikken Koza 1 (New Biochemistry Experimental Lectures 1 in English), Protein IV" (1992), edited by The Japanese Biochemical Society, Tokyo Kagaku Dojin Co., Ltd., Tokyo, Japan). Alternatively, a peptide of the present invention may be produced by a genetic recombination method using a nucleic acid encoding the peptide or a phage display method. For example, DNA encoding the amino acid sequence of a peptide of the present invention is inserted into expression vectors, which is then introduced into host cells. The host cells can be cultured to produce the peptide of interest. The produced peptide can be collected or purified by a routine method, for example, chromatography (e.g., gel filtration chromatography, ion-exchange column chromatography, affinity chromatography, reverse-phase column chromatography, or HPLC), ammonium sulfate fractionation, ultrafiltration, or immunoadsorption.

For peptide synthesis, protected amino acids, in which functional groups other than α-amino and α-carboxyl groups to be bound in each amino acid have been protected, are prepared. The α-amino group of one amino acid is reacted with the α-carboxyl group of another amino acid to form a peptide bond. Typically, the carboxyl group of the amino acid residue to be positioned at the C terminus of the peptide is bound in advance with a solid phase via an appropriate spacer or linker. The protective group at the amino terminus of the dipeptide thus obtained is selectively removed, and the amino terminus forms a peptide bond with the α-carboxyl group of a subsequent amino acid. This operation is continuously performed to produce a peptide having protected side groups. Finally, all the protective groups are removed, and the resulting peptide is separated from the solid phase. The details of the types of the protective groups, protection methods, and peptide binding methods are specifically described in the above-mentioned literatures.

The genetic recombination method comprises inserting DNA encoding a peptide of the present invention into appropriate expression vectors, introducing the vectors into appropriate host cells, culturing the cells, and collecting the peptide of interest from within the cells or from extracellular fluids. Examples of the vectors include, but are not limited to, plasmids, phages, cosmids, phagemids, and viral vectors.

Examples of the plasmid vectors include, but are not limited to, E. coli-derived plasmids (e.g., pET22b (+), pBR322, pBR325, pUC118, pUC119, pUC18, pUC19, and pBluescript), Bacillus subtilis-derived plasmids (e.g., pUB110 and pTP5), and yeast-derived plasmids (e.g., YEp13 and YCp50). Examples of the phage vectors include, but are not limited to, T7 phage display vectors (T7Select 10-3b, T7Select 1-1b, T7Select 1-2a, T7Select 1-2b, T7Select 1-2c, etc. (Novagen)) and λ phage vectors (Charon 4A, Charon 21A, EMBL3, EMBL4, λgt10, λgt11, λZAP, λZAP II, etc.). Examples of the viral vectors include, but are not limited to, animal viruses such as retrovirus, adenovirus, adeno-associated virus, vaccinia virus, and hemagglutinating virus of Japan, and insect viruses such as baculovirus. Examples of the cosmid vectors include, but are not limited to, Lorist 6. Charomid 9-20, and Charomid 9-42. Examples of the known phagemid vectors include, but are not limited to, pSKAN, pBluescript, pBK, and pComb3H. Each vector may contain, for example, regulatory sequences that allow the expression of the DNA of interest, a selection marker for screening for a vector containing the DNA of interest, and multicloning site for inserting therein the DNA of interest. Such regulatory sequences encompass promoters, enhancers, terminators, S-D sequences or ribosomal binding sites, replication origins, poly-A sites, and the like. For example, an ampicillin resistance gene, a neomycin resistance gene, a kanamycin resistance gene, a dihydrofolate reductase gene, or the like may be used as a selection marker. The host cells to which the vectors are introduced are, for example, bacteria such as E. coli or Bacillus subtilis, yeast cells, insect cells, animal cells (e.g., mammalian cells), or plant cells. These cells are transformed or transfected by a method, such as a calcium phosphate, electroporation, lipofection, particle gun, or PEG method. The transformed cells are cultured according to a method usually used in the culture of host organisms. For example, microbes such as E. coli or yeast cells are cultured in a medium containing a carbon source, a nitrogen source, inorganic salts, etc., assimilable by the host microbes. For easily collecting the peptide of the present invention, it is preferred to extracellularly secrete the peptide produced by expression. For this purpose, DNA encoding a peptide sequence that allows peptide secretion from the cells is bound to the 5' end of the DNA encoding the peptide of interest. A fusion peptide transferred to the cell membrane is cleaved by signal peptidase to secrete and release the peptide of interest into the medium. Alternatively, the intracellularly accumulated peptide of interest may be collected. In this case, the cells are physically or chemically disrupted, and the peptide of interest is collected therefrom using a protein purification technique.

Thus, the present invention further relates to a nucleic acid encoding a peptide of the present invention. In this context, the nucleic acid encompasses DNA and RNA (e.g., mRNA).

A peptide of the present invention may be labeled in order to achieve the detection of IgA. Examples of the label include, but are not limited to, fluorescent dyes, chemiluminescent dyes, enzymes, radioisotopes, fluorescent proteins, and biotin. Preferable examples of the label include fluorescein, fluorescein derivatives such as FITC, rhodamine, rhodamine derivatives such as tetramethylrhodamine, and fluorescent dyes such as Texas Red.

A peptide of the present invention may be fused with an arbitrary protein. For example, a fluorescent protein such as GFP (green fluorescent protein) or an enzyme such as peroxidase may be used as the protein and can also be used as a label. In this case, the peptide of the present invention and the protein can be prepared as a fusion protein, if necessary via an appropriate linker, by a genetic recombination method. In this context, the fusion protein should be prepared without impairing the ability of the peptide of the present invention to bind human IgA.

A peptide of the present invention may further be immobilized on a solid phase capable of filling in an affinity column so that it can be used in the separation, purification, analysis, etc. of human IgA.

Preferable examples of the solid phase used for peptide immobilization include, but not limited to, polystyrene, polyethylene, polypropylene, polyester, polyacrylonitrile, styrene-butadiene copolymers, (meth)acrylic acid ester polymers, fluoropolymers, silica gels, saccharides (e.g., cross-linked dextran, polysaccharide, and agarose), glass, metals, magnetic materials, and combinations thereof. The form of such a solid phase may be any form, for example, trays, spheres, fibers, particles, rods, flat plates, containers, cells, microplates, test tubes, films or membranes, gels, or chips, etc. Specific examples thereof include magnetic beads, glass beads, polystyrene beads, Sepharose beads, silica gel beads, polysaccharide beads, polystyrene plates, glass plates, and polystyrene tubes. The peptide of the present invention can be immobilized onto these solid phases using a method well known by those skilled in the art, for example, a physical adsorption, covalent bond, or ionic bond method, etc. The immobilization is preferably performed through a covalent bond. The solid phase has, on its surface, a chemical functional group(s) (e.g., hydroxy, amino, and N-hydroxysuccinimidyl groups), preferably a chemical functional group(s) having an alkylene chain having approximately 4 to 20 carbon atoms as a spacer, and this functional group is chemically reacted with the carboxy terminus of the peptide to form an ester bond or an amide bond, etc. The solid phase with the immobilized peptide of the present invention can be filled in a column such as an affinity chromatography column or an HPLC column and used for the detection, purification, or separation of human IgA.

(Method for Purifying IgA)

The present invention further provides a method for purifying IgA, comprising: binding the peptide or immobilized peptide of the present invention to IgA; and releasing bound IgA to collect the IgA.

The solid phase with the immobilized peptide of the present invention is filled in a column such as an affinity chromatography column or an HPLC column. The column is equilibrated with an appropriate buffer. A solution containing human IgA is applied thereto at room temperature to 0° C., preferably at a low temperature of approximately 10° C. to 0° C. (more preferably approximately 4° C.) to bind the human IgA to the peptide on the solid phase. For example, for separation of IgA from serum, the serum can be applied to the column using a buffer having a neutral pH, for example, pH 6.0 to 7.5, to perform the binding operation. A buffer having a pH in the acidic range, for example, pH 2 to 4 (e.g., a 0.2 M glycine-HCl buffer (pH 3.5 to pH 2.5) containing 0.3 M NaCl) can be flowed in the column to elute IgA.

The successful collection of IgA can be determined by, for example, electrophoresis and subsequent Western blotting using anti-human IgA antibodies. The electrophoresis conditions can involve SDS-PAGE using 5 to 20% acrylamide gradient gels. The Western blotting conditions can involve transferring the proteins thus electrophoresed to a PVDF membrane and blocking the membrane with skim milk, followed by detection using anti-human IgA α-chain goat antibodies and HRP-labeled anti-goat IgG mouse antibodies.

The method of the present invention is useful for obtaining an IgA-rich fraction in the step of purifying IgA from IgA-containing products formed by various methods. As such, the method of the present invention is preferably used in column chromatography such as affinity chromatography or HPLC. For IgA purification, such a chromatography method as well as protein purification techniques routinely used, for example, chromatography (e.g., gel filtration chromatography, ion-exchange column chromatography, or reverse-phase column chromatography), ammonium sulfate fractionation, ultrafiltration, and the like can be combined appropriately.

(Method for Analyzing IgA)

The present invention further provides a method for detecting IgA, comprising binding the peptide or immobilized peptide of the present invention to IgA in a sample and detecting bound IgA. In this context, the detection encompasses either of qualitative and quantitative analyses.

For IgA detection, the sample is bound to a membrane, a polystyrene well plate, or the like while a buffer suitable for the operation is used. The resulting membrane or plate is contacted with the labeled peptide of the present invention and washed, if necessary. Then, the level of the label can be analyzed qualitatively or quantitatively.

Alternatively, the HPLC column with the immobilized peptide of the present invention as described above may be used. In this case, a sample containing human IgA is injected to the column, and the human IgA is bound to the peptide by flowing a binding buffer. The bound protein is detected and recorded using, for example, absorbance at 280 nm or fluorescence at 350 nm emitted by excitation at 280 nm, and eluted from the column using an elution buffer (e.g., by gradient elution from 0 M NaCl to 0.15 M NaCl in a 0.1 M glycine-HCl buffer (pH 2.5)). IgA can be analyzed qualitatively or quantitatively from the obtained peak and peak area.

(Kit and Column)

The present invention further provides a kit for analysis (qualitative, quantitative, etc.) or purification of human IgA, comprising at least one peptide or immobilized peptide of the present invention.

Individual peptides or immobilized peptides contained in the kit of the present invention are separately housed in containers. If necessary, the kit may also contain an instruction manual which describes procedures of analyzing or purifying human IgA. The kit may further contain reagents or buffers necessary for analysis, an immobilized peptide-packed column, etc.

The present invention further provides a column for IgA separation, comprising the immobilized peptide of the present invention.

The immobilized peptide may be prepared generally by covalently or non-covalently binding the peptide to a carrier (or a filler or a packing material) for chromatography. Examples of such a carrier include polysaccharide- (e.g., agarose- or Sepharose-) based carriers, silica gel-based carriers, and resin- or polymer-based carriers. The peptide may be bound to the carrier via a spacer such as a hydrocarbon chain (e.g., C4 to C16).

The IgA separation column is a column for separating IgA and specifically encompasses columns such as chromatography columns or high-performance liquid chromatography (HPLC) columns for analysis, purification, or fractionation of IgA. The size of the column is not particularly limited and may vary depending upon its use (e.g., for analysis or for purification or fractionation), the amount applied (loaded) or injected, and the like. The column may be made of a material usually used for columns, such as metals, plastics, or glass.

The column can be produced by densely packing or filling the immobilized peptide of the present invention (in a dry or wet state) prepared according to the approach described above into the column.

EXAMPLES

Hereinafter, the present invention will be described more specifically with reference to Examples. However, the scope of the present invention is not intended to be limited to these Examples.

Example 1

Isolation of Human IgA-Specific Phage from Random Peptide T7 Phage Library

In order to isolate human IgA-specific phages from a random peptide library ($CX_{7-10}C$ and $X_3CX_{7-10}CX_3$) using a previously constructed T7 phage display system, the following approach of biopanning was used: a solution of $5 \times 10^{10}$ pfu T7 phage library (i.e., a mixture of $CX_{7-10}C$ and $X_3CX_{7-10}CX_3$) in PBS containing 0.5% BSA was added to wells of a 96-well microplate (Nunc, Maxisorp) coated with human IgG (polyclonal, ICN/Cappel Biomedicals) (1 μg/100 μl/well) and blocked with 0.5% BSA, followed by reaction for 1 hour (absorption step). The supernatant was then transferred to wells coated with human IgA (From human plasma, Athens Research & Technology, Athens, Ga., USA) (1 μg/100 μl/well) and blocked with 0.5% BSA (bovine serum albumin), followed by 1-hour reaction (binding step). After removal of the supernatant phage solution, the wells were washed five times with PBS (phosphate-buffered saline) containing 0.1% Tween® (washing step). A culture solution (300 μl) of E. coli 5615 (Novagen) was added thereto for infection, and the phages were incubated together with 3 ml of the E. coli culture solution at 37° C. until phage amplification and E. coli lysis were completed (amplification step). From the culture solution after the lysis, phages were collected by phage precipitation using polyethylene glycol according to a standard method. The obtained phages were dissolved in PBS, passed through a 0.45-μm filter, and then used in the subsequent rounds of panning. Panning was performed 5 times (including the round described above) to enrich IgA-specific phages. In the 3rd to 5th rounds of panning, wells coated with human IgG and mouse IgE (1 μg/well each) were used in the absorption step, and the wells were washed 10 times with PBS containing 0.3% Tween© in the washing step.

The phages obtained after the 5 rounds of panning were examined by ELISA for their binding specificity for various immunoglobulins. As a result, as shown in FIG. 1, apparent enhancement in activity for binding to human IgA was observed, compared with results of ELISA using the original library.

Thus, 20 of these phages were cloned at random. After the cloning, 10 clones that exhibited binding activity in ELISA were analyzed for their peptide motifs displayed thereon to determine the amino acid sequences (Table 1).

TABLE 1

Peptide motif displayed by human IgA-specific phage

| Library | Clone name | Sequence 1    10    18 | Frequency of appearance |
|---|---|---|---|
| XCX9CX | hA-1 | STFCLLGQK-DQSYCFTI (SEQ ID NO: 12) | 2/20 |
| XCX8CX | hA-2 | HMRCLHYK-GRRVCFLL (SEQ ID NO: 1) | 5/20 |
| XCX8XCX | hA-3 | KTMCLRYN-HDKVCFRI (SEQ ID NO: 3) | 2/20 |
| XCX10CX | hA-4 | LVLCLVHRTSKHRKCFVI (SEQ ID NO: 14) | 1/20 |

Four motifs (hA-1, hA-2, hA-3, and hA-4) were obtained as to the obtained peptides. Of the obtained motifs, hA-2 exhibited the highest frequency of appearance. The comparison of the amino acid sequences among the obtained motifs showed that completely conserved residues except for Cys introduced during library design were Leu5 and Phe16 and had a trend toward a hydrophobic residue at the 18th position.

Figure 2:
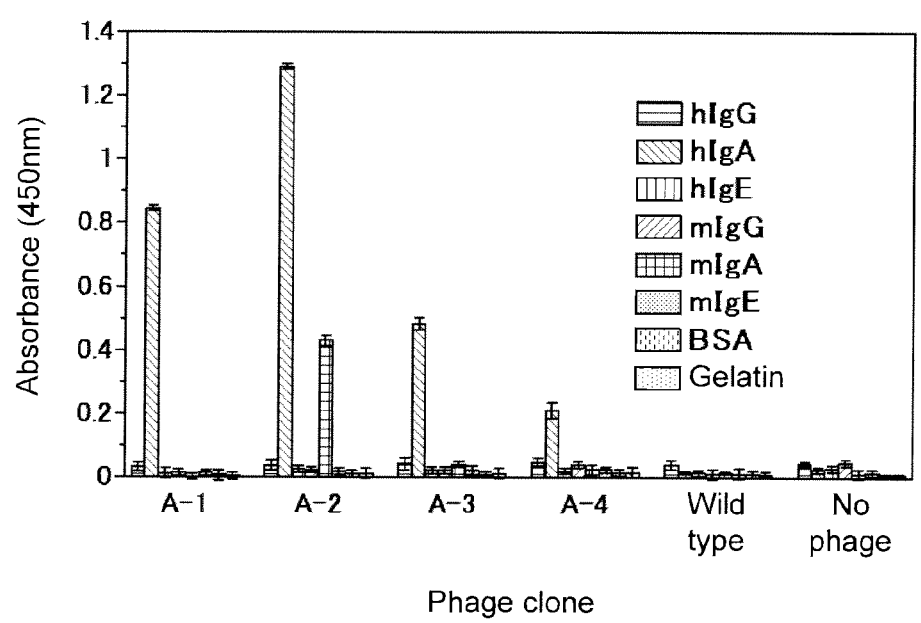
FIG. 2 shows the binding specificity, measured by ELISA, of human IgA-binding phage clones.

Results obtained by examining the cloned phages (hA-1, hA-2, hA-3, and hA-4) for their binding properties for various immunoglobulins are shown in FIG. 2. All of the clones exhibited specificity for human IgA. The hA-2 clone also exhibited the activity of binding to mouse IgA.

In order to analyze important residues in the obtained IgA-specific peptide motifs, a mutant library based on the hA-2 motif having the highest binding strength was prepared as follows: nucleotides encoding residues other than the Cys residues at amino acid Nos. 4 and 13 in a nucleotide sequence (SEQ ID NO: 45) encoding the hIgA-2 peptide motif (SEQ ID NO: 1) of FIG. 3 were synthesized using a nucleotide mixture. A peptide library was prepared therefrom so that the peptides had partially a random amino acid(s) (sequence diversity of the library: $1.4 \times 10^7$). The nucleotide mixture was prepared so that it consisted of the original nucleotide sequence 70% and the remaining 3 nucleotides 10% each, resulting in the original codons appearing with theoretically 35% probability.

Figure 4:
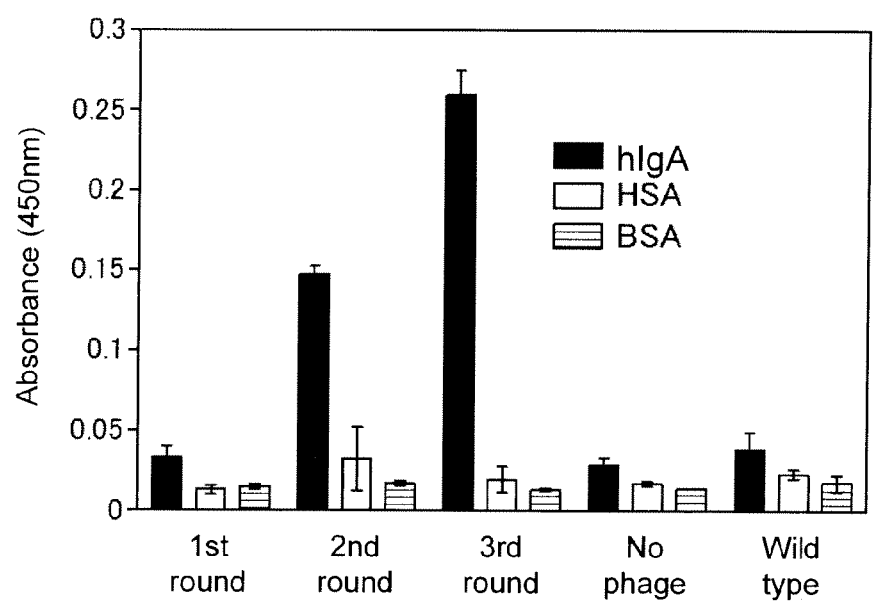
FIG. 4 shows the enrichment of a human IgA-specific phage from a partial mutant library.

This partial mutant library was used in panning for hIgA to enrich specific phages. As shown in FIG. 4, the enrichment of the IgA-binding phages was seen from the 2nd round, and the binding activity was further enhanced after the 3rd round. Thus, the phages after the 3rd round were cloned, and 21 clones were evaluated by ELISA for their binding activity.

As a result, 10 clones exhibited binding activity and were analyzed for their displayed motifs, thereby obtaining the motifs having amino acid sequences as shown in Table 2. Interestingly, the residues at amino acid Nos. 5, 7, 9, and 12 in the hA-2 motif were completely conserved, suggesting their importance for binding. Also, the residues at amino acid Nos. 14 and 16 were all hydrophobic, suggesting the importance of hydrophobic interaction for this region. By contrast, the residues at amino acid No. 8 were all basic amino acid residues, from which the presence of interaction with a negative charge of the antibody was presumed. These amino acid numbers are amino acid numbers based on 16 amino acid residues (which, in the case that the number of amino acid residues of the peptide is regarded as 18 amino acid residues, are 16 amino acid residues except for the deleted 9th and 10th residues), as shown in Table 2.

TABLE 2

Human IgA-specific peptide motif obtained from partial mutant library of hA-2 motif

| | 1 | | | | 5 | | | | | 10 | | | | | 15 | | |
|---|---|---|---|---|---|---|---|---|---|---|---|---|---|---|---|---|---|
| hIgA2-4 | Q | M | R | C | L | S | Y | K | G | R | R | V | C | L | W | L | (SEQ ID NO: 2) |
| hIgA2-6 | H | K | R | C | L | H | Y | R | G | R | M | V | C | F | L | I | (SEQ ID NO: 3) |
| hIgA2-15 | K | R | L | C | L | Q | Y | K | G | S | K | V | C | F | R | L | (SEQ ID NO: 4) |
| hIgA2-18 | R | M | R | C | L | T | Y | R | G | R | R | V | C | L | E | L | (SEQ ID NO: 5) |
| hIgA2-21 | S | M | R | C | L | Q | Y | R | G | S | R | V | C | L | T | L | (SEQ ID NO: 6) |
| hIgA2-2 | Q | K | R | C | L | K | Y | K | G | S | R | V | C | F | F | L | (SEQ ID NO: 7) |
| hIgA2-6 | H | L | R | C | L | R | Y | K | G | T | R | V | C | F | S | L | (SEQ ID NO: 8) |
| hIgA2-9 | H | V | R | C | L | S | Y | K | G | R | E | V | C | V | Q | L | (SEQ ID NO: 9) |
| hIgA2-17 | P | R | M | C | L | H | Y | K | G | R | R | V | C | I | P | Y | (SEQ ID NO: 10) |
| hIgA2-16 | H | V | R | C | L | R | Y | R | G | K | N | V | C | F | L | L | (SEQ ID NO: 11) |

The respective amino acid sequences of the hA-2 peptide motifs shown in Table 2 are represented by SEQ ID NOs: 2, 3, 4, 5, 6, 7, 8, 9, 10, and 11 in Sequence Listing in the order in which they appear (i.e. in the order of hIgA2-4, hIgA2-6, hIgA2-15, hIgA2-18, hIgA2-21, hIgA2-2, hIgA2-6, hIgA2-9, hIgA2-17, and hIgA2-16).

Figure 5:
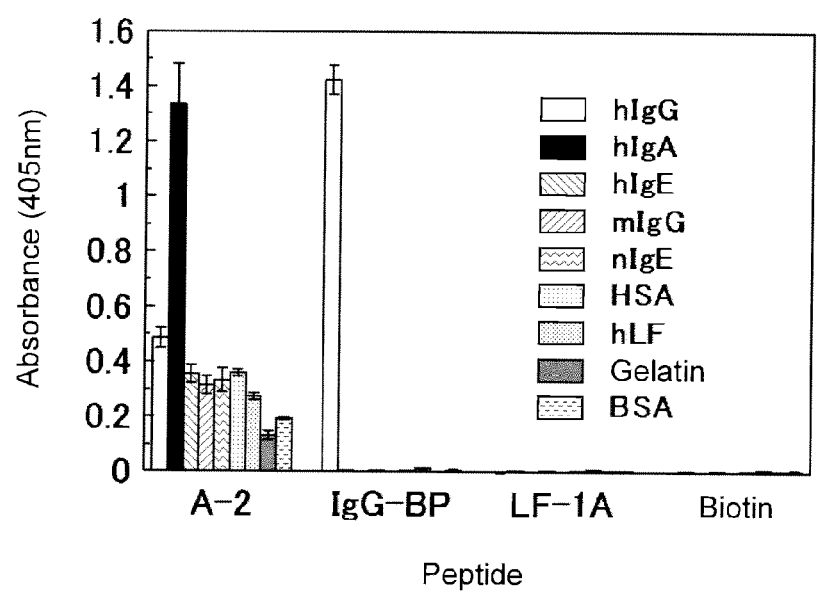
FIG. 5 shows the binding specificity of a synthetic hIgA-2 peptide. In this figure, IgG-BP represents a peptide specific for human IgG, and LF-A1 represents a peptide specific for human lactoferrin.

A peptide based on the hIgA-2 peptide motif was synthesized and evaluated for its binding specificity. The peptide used was tagged at its N terminus with a biotinylated (PEG)$_4$ group. A 1:4 (molar ratio) mixture of AP-labeled streptavidin and the peptide (7.5 nM and 30 nM, respectively) was added to wells of a microplate with each target protein immobilized (50 ng/well), and reacted therewith. The wells were washed five times with PBS-T (i.e., PBS-Tris), and binding was then detected by a chromogenic method using PNP-phosphate as a substrate. The results are shown in FIG. 5. The hIgA-2 peptide was confirmed to strongly bind particularly to human IgA, though it also slightly bound to other proteins.

Figure 6:
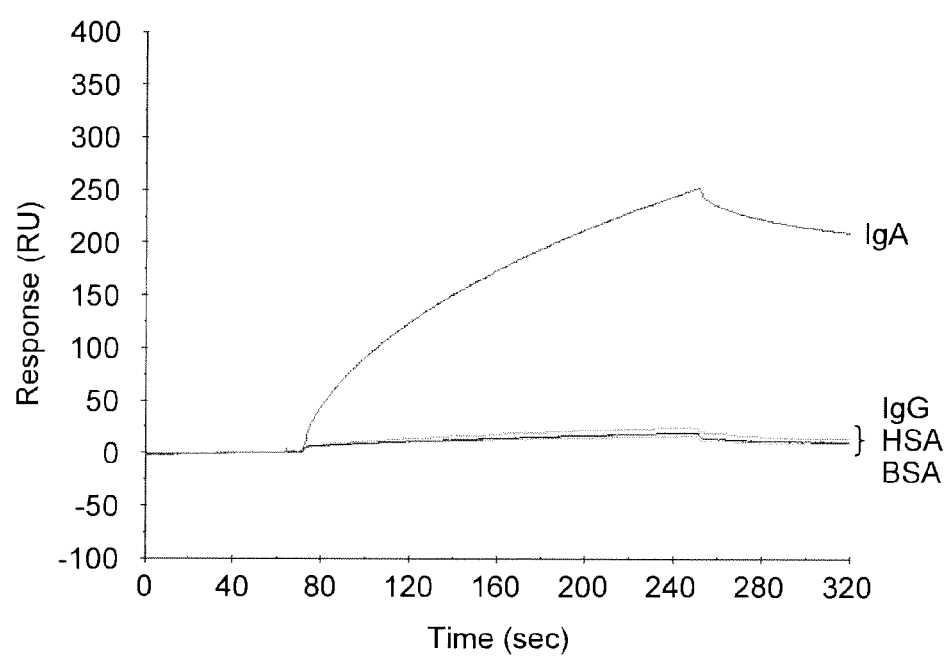
FIG. 6 shows the results of surface plasmon analysis of the binding of the synthetic hIgA-2 peptide to human IgA.

In order to further confirm the specificity of this binding, the binding strength was evaluated by surface plasmon resonance analysis using ProteOn XPR36 (Bio-Rad) (FIG. 6).

Example 2

Purification of Human IgA Using hIgA-2 Peptide

Figure 7:
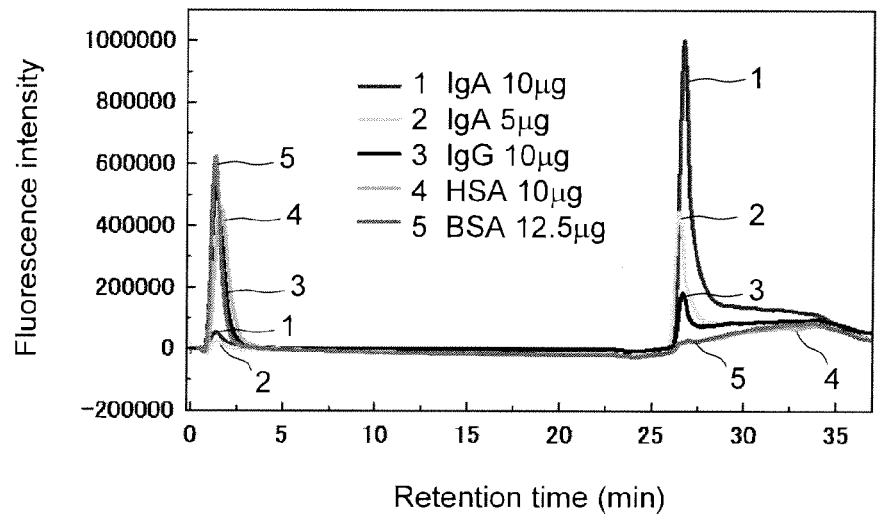
FIG. 7 shows the specific adsorption and elution of human IgA using an hIgA-2 peptide-immobilized column.

In order to study whether the hIgA-2 peptide functions as a ligand for purification of human IgA, biotinylated (PEO)$_4$-hIgA-2 was immobilized on 1 ml of HiTrap Streptavidin HP (GE Healthcare). Various proteins were injected thereto, and the binding ability thereof was evaluated (FIG. 7). Human IgG, HAS (human serum albumin), and BSA (bovine serum albumin) used as control proteins substantially flowed through the column, whereas IgA (5 or 10 μg) was adsorbed on the column and eluted from the column by gradient elution from PBS to 0.2 M glycine-HCl (pH 2.5)

containing 0.3 M NaCl after washing with PBS. This demonstrated that the hIgA-2 peptide had a basic performance in terms of specificity and binding ability as a ligand for purification of human IgA.

Figure 8:
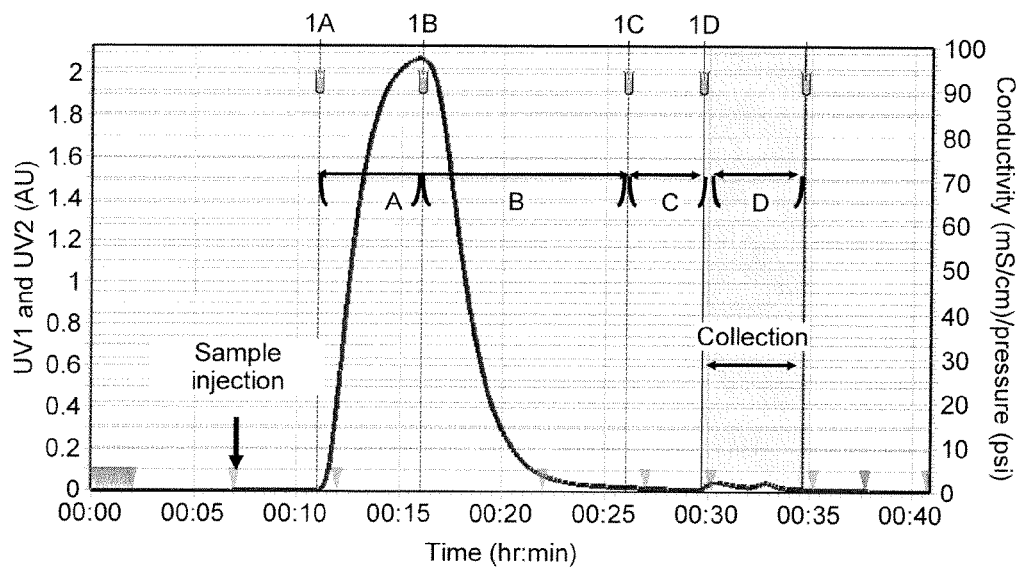
FIG. 8 shows the purification of IgA from human serum using the hIgA-2 peptide-immobilized column.

In order to further study the usefulness of the hIgA-2 peptide-immobilized column, IgA was purified from human serum. One (1) ml of human serum was diluted 5-fold with PBS and then applied to the column connected with Profinia Protein Purification System (Bio-Rad). After washing with PBS, bound proteins were eluted with 0.2 M glycine-HCl (pH 3.5) containing 0.3 M NaCl and subsequently with 0.2 M glycine-HCl (pH 2.5) containing 0.3 M NaCl (FIG. 8).

Figure 9:
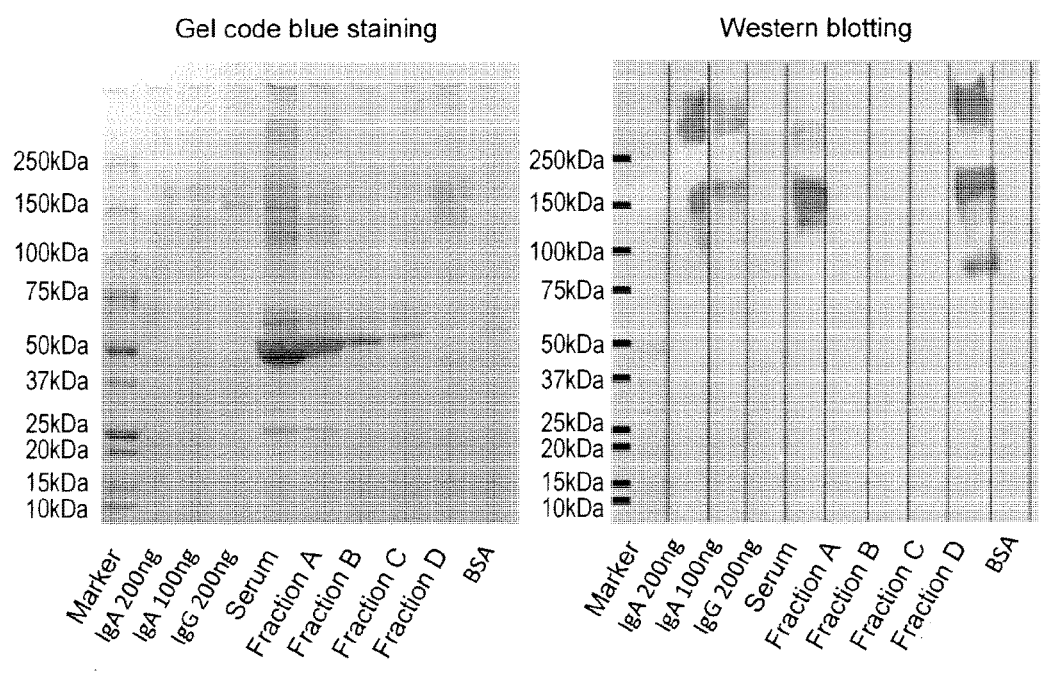
FIG. 9 shows the results of SDS-PAGE (left panel) and Western blotting (right panel) of IgA collected from the hIgA-2 peptide-immobilized column.

Each fraction eluted by chromatography was analyzed by SDS-PAGE and Western blotting using anti-human IgA antibodies (FIG. 9). The acidic elution fraction (fraction D) was detected as a smear band spanning from 130 to 180 kDa substantially similar to the IgA protein preparation by protein staining after SDS-PAGE. By contrast, in the Western blotting using anti-human IgA antibodies, both the serum and the standard IgA preparation exhibited a smear band at a position of 300 kDa or more, in addition to the above-described 130 to 180 kDa band. Such two bands probably appeared, because IgA in serum is mainly composed of serum IgA (monomer) but contains, as a minor component, a dimer (secretory form) formed via linkage of J-chain. Likewise, these two bands were detected in the fraction D eluted from the column. This demonstrated that the hIgA-2 peptide-immobilized column was able to be used for purification of both serum and secretory forms. Substantially no IgA-derived band was detected in the flow-through fraction A and the wash fractions B and C, demonstrating that most of the IgA in serum was collected by this chromatography.

These results showed that related peptides including the hIgA-2 peptide isolated this time were specific for human IgA and were highly useful as affinity ligands for purification. Such a low-molecular-weight (molecular weight: approximately 2000) ligand for purification or detection of human IgA was reported for the first time and is useful not merely as a reagent for detection or purification of human IgA but also as a standard purification system for human IgA antibody drugs that can be expected as new antibody drugs in the future.

Example 3

Peptides Having A-3 Peptide Motifs Exhibiting High Affinity for hIgA

The residues at amino acid Nos. 5, 7, 9, and 12 in the peptide consisting of 16 amino acids (which, in the case that the number of amino acid residues of the peptide is regarded as 18 amino acid residues, are 16 amino acid residues except for the deleted 9th and 10th residues) were considered important for binding to IgA from the results of panning using the partial mutant library shown in Example 2. Thus, in order to search for a sequence having higher affinity, an optimized library was prepared in the same way as in Example 1 so that these amino acids were fixed while the other amino acids appeared at random (FIG. 10).

Figure 11:
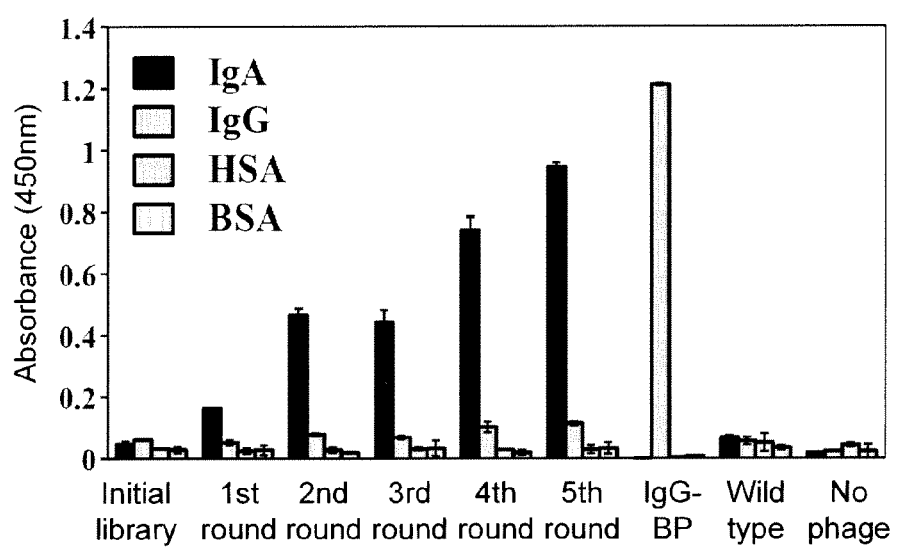
FIG. 11 shows the enrichment of an hIgA-specific phage by panning from the optimized library.

This library was again used in panning for hIgA to enrich specific phages having high affinity for hIgA. As shown in FIG. 11, the enrichment of the hIgA-binding phages was seen from the 2nd round, and the binding activity was further enhanced after the 5th round. Thus, the phages after the 5th round were cloned, and 29 clones of the phages excellent in binding activity were evaluated by ELISA for their binding specificity.

Figure 12:
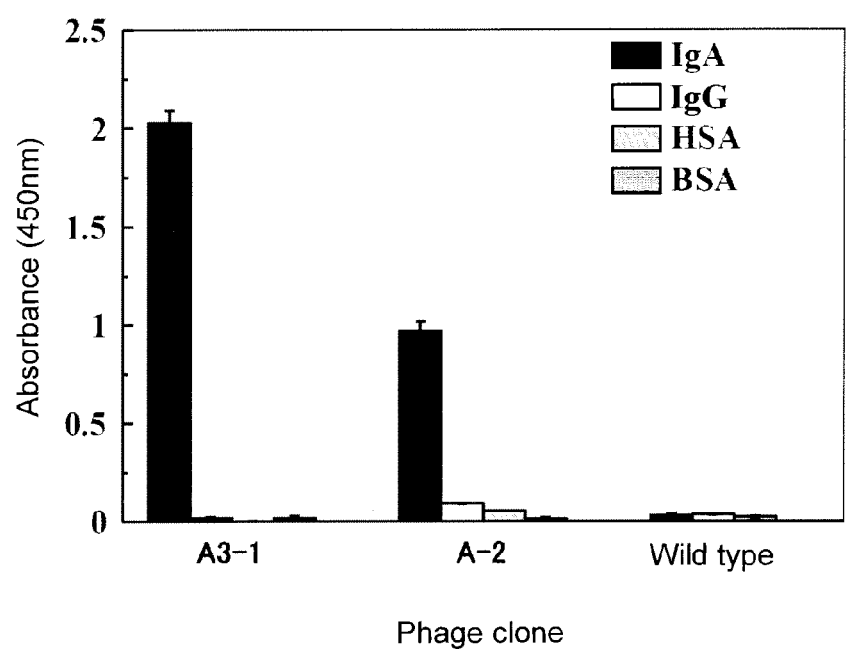
FIG. 12 shows the binding specificity measured by ELISA of the A3-1-displayed phage clone for hIgA.

As a result, A3-1 peptide (consisting of 16 amino acid residues) having higher binding specificity and binding activity than those of the A-2 peptide was obtained (FIG. 12). As a result of analyzing the amino acid sequences displayed by the clones exhibiting the binding activity, each amino acid site in the obtained motifs had an appearance tendency as shown in Table 3.

TABLE 3

| Peptide | Sequence | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| A3-1 | S | | D | | V | | C | L | R | | Y | R | G | R | | P | | V | C | F | | Q | | V | |
| Frequency of amino acid appearance | R | 24 | A | 24 | V | 45 | C | L | N | 24 | Y | R | 93 | G | R | 55 | P | 41 | V | C | F | 52 | R | 24 | W | 24 |
| | S | 17 | D | 14 | R | 17 | | | S | 17 | | N | 3 | | S | 21 | R | 14 | | | R | 34 | Q | 14 | F | 17 |
| | P | 14 | L | 14 | I | 10 | | | K | 14 | | Q | 3 | | K | 14 | Q | 14 | | | L | 3 | T | 10 | V | 14 |
| | L | 10 | R | 10 | L | 7 | | | R | 14 | | | | | A | 7 | T | 10 | | | M | 3 | I | 10 | P | 10 |
| | G | 10 | S | 7 | W | 7 | | | M | 10 | | | | | N | 3 | K | 7 | | | G | 3 | K | 7 | G | 7 |
| | T | 10 | E | 7 | A | 3 | | | A | 3 | | | | | | | F | 3 | | | | | V | 7 | I | 7 |
| | V | 7 | V | 7 | T | 3 | | | T | 3 | | | | | | | V | 3 | | | | | N | 3 | L | 7 |
| | F | 3 | F | 3 | F | 3 | | | D | 3 | | | | | | | S | 3 | | | | | L | 3 | R | 3 |
| | H | 3 | W | 3 | S | 3 | | | Q | 3 | | | | | | | L | 3 | | | | | F | 3 | T | 3 |
| | | | M | 3 | | | | | H | 3 | | | | | | | | | | | | | P | 3 | Y | 3 |
| | | | | | | | | | G | 3 | | | | | | | | | | | | | D | 3 | | |
| | | | | | | | | | | | | | | | | | | | | | | | H | 3 | | |
| | | | | | | | | | | | | | | | | | | | | | | | M | 3 | | |

In order to confirm the importance of the amino acid residues with high frequency of appearance for binding to hIgA, the amino acids with high frequency and the amino acids seen in the A-2 peptide were introduced into the sequence of the A3-1 peptide. At the same time, in order to examine the importance of the side chain of each residue, alanine scanning was performed. Each amino acid substitution variant was evaluated for its affinity for hIgA by surface plasmon resonance analysis using Biacore T100 (GE Healthcare). Each chemically synthesized peptide was analyzed using the hIgA-immobilized CM5 sensor chip. The affinity of each substitution variant for hIgA was calculated on the basis of the obtained sensorgram.

The substitution variants having alanine (A) at amino acid No. 5, 7, 9, or 12, of the peptides of 16 amino acids (see Table 4 below) considered important from the results of the partial mutant library, had a reduced strength of binding to IgA. From this fact, the importance of the residues was reconfirmed. Particularly, the substitutions at amino acid Nos. 5 and 7 remarkably decreased the binding strength, suggesting that the residues were very important for binding to hIgA. Also, each substitution variant having a substitution at amino acid No. 1, 2, 6, 15, or 16 exhibited improvement in affinity for hIgA, compared with the A3-1 peptide. The results are shown in Table 4. In this context, the respective amino acid sequences of the A3-1 peptides (A3-1, A3-1 (S1R), A3-1(S1H) . . . A3-1(V16A), A3-1(opt1), and A3-1 (Opt2)) of Table 4 are represented by SEQ ID NOs: 15, 16, 17 . . . 42, 43, and 44 in this order in Sequence Listing.

Figure 13:
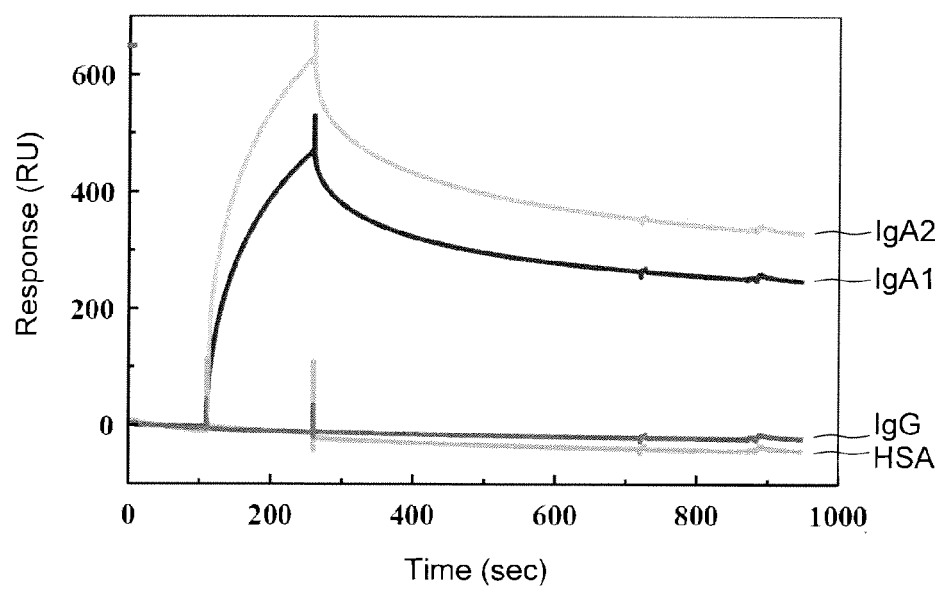
FIG. 13 shows the results of surface plasmon resonance analysis of the binding of a synthetic A3-1(Opt2) peptide to human IgA.

Healthcare) (FIG. 13). The A3-1(Opt2) peptide had high specificity for hIgA, as in the A-2 peptide and the A3-1 peptide, and was confirmed to have a slightly higher binding strength to hIgA2 than that to hIgA1 as a result of evaluating the strength of binding to hIgA1 and hIgA2.

The A3-1(Opt2) peptide had approximately 52 times the affinity of the A-2 peptide. Thus, an A3-1(Opt2) peptide

TABLE 4

| Peptide | 1 | 2 | 3 | 4 | 5 | 6 | 7 | 8 | 9 | 10 | 11 | 12 | 13 | 14 | 15 | 16 | | Kd [μM] |
|---|---|---|---|---|---|---|---|---|---|---|---|---|---|---|---|---|---|---|
| A-2 | H | M | R | C | L | H | Y | K | G | R | R | V | C | F | L | L | (SEQ ID NO: 1) | 1.3 |
| A3-1 | S | D | V | C | L | R | Y | R | G | R | P | V | C | F | Q | V | (SEQ ID NO: 15) | 0.53 |
| A3-1 (S1R) | R | | | | | | | | | | | | | | | | (SEQ ID NO: 16) | 0.41 |
| A3-1 (S1H) | H | | | | | | | | | | | | | | | | (SEQ ID NO: 17) | 0.36 |
| A3-1 (S1A) | A | | | | | | | | | | | | | | | | (SEQ ID NO: 18) | 2.0 |
| A3-1 (D2M) | | M | | | | | | | | | | | | | | | (SEQ ID NO: 19) | 0.15 |
| A3-1 (D2A) | | A | | | | | | | | | | | | | | | (SEQ ID NO: 20) | 0.25 |
| A3-1 (V3R) | | | R | | | | | | | | | | | | | | (SEQ ID NO: 21) | 3.0 |
| A3-1 (V3A) | | | A | | | | | | | | | | | | | | (SEQ ID NO: 22) | 3.0 |
| A3-1 (L5A) | | | | | A | | | | | | | | | | | | (SEQ ID NO: 23) | 20 |
| A3-1 (R6N) | | | | | | N | | | | | | | | | | | (SEQ ID NO: 24) | 0.76 |
| A3-1 (R6H) | | | | | | H | | | | | | | | | | | (SEQ ID NO: 25) | 0.43 |
| A3-1 (R6A) | | | | | | A | | | | | | | | | | | (SEQ ID NO: 26) | 0.34 |
| A3-1 (Y7A) | | | | | | | A | | | | | | | | | | (SEQ ID NO: 27) | 25 |
| A3-1 (R8A) | | | | | | | | A | | | | | | | | | (SEQ ID NO: 28) | 4.4 |
| A3-1 (G9A) | | | | | | | | | A | | | | | | | | (SEQ ID NO: 29) | 1.9 |
| A3-1 (R10S) | | | | | | | | | | S | | | | | | | (SEQ ID NO: 30) | 1.7 |
| A3-1 (R10A) | | | | | | | | | | A | | | | | | | (SEQ ID NO: 31) | 2.2 |
| A3-1 (P11R) | | | | | | | | | | | R | | | | | | (SEQ ID NO: 32) | 5.2 |
| A3-1 (P11A) | | | | | | | | | | | A | | | | | | (SEQ ID NO: 33) | 4.4 |
| A3-1 (V12A) | | | | | | | | | | | | A | | | | | (SEQ ID NO: 34) | 4.0 |
| A3-1 (F14R) | | | | | | | | | | | | | | R | | | (SEQ ID NO: 35) | 2.3 |
| A3-1 (F14A) | | | | | | | | | | | | | | A | | | (SEQ ID NO: 36) | 11 |
| A3-1 (Q15R) | | | | | | | | | | | | | | | R | | (SEQ ID NO: 37) | 0.31 |
| A3-1 (Q15L) | | | | | | | | | | | | | | | L | | (SEQ ID NO: 38) | 0.36 |
| A3-1 (Q15A) | | | | | | | | | | | | | | | A | | (SEQ ID NO: 39) | 0.28 |
| A3-1 (V16W) | | | | | | | | | | | | | | | | W | (SEQ ID NO: 40) | 1.6 |
| A3-1 (V16L) | | | | | | | | | | | | | | | | L | (SEQ ID NO: 41) | 0.45 |
| A3-1 (V16A) | | | | | | | | | | | | | | | | A | (SEQ ID NO: 42) | 0.82 |
| A3-1 (Opt1) | H | M | V | C | L | A | Y | R | G | R | P | V | C | F | A | L | (SEQ ID NO: 43) | 0.044 |
| A3-1 (Opt2) | H | M | V | C | L | S | Y | R | G | R | P | V | C | F | S | L | (SEQ ID NO: 44) | 0.025 |

Of the peptides shown in Table 4, particularly, the peptides having a dissociation constant (Kd) less than 1 μM in binding with human IgA have the amino acid sequences of SEQ ID NOs: 15, 16, 17, 19, 20, 24, 25, 26, 37, 38, 39, 41, and 42 and had high affinity for human IgA.

Peptides containing an amino acid exhibiting the highest improvement in affinity at each amino acid site in the peptide consisting of 16 amino acids were further designed on the basis of these results. Specifically, A3-1(Opt1) peptide (SEQ ID NO: 43) containing a histidine residue at amino acid No. 1, a methionine residue at amino acid No. 2, an alanine residue at amino acid No. 6, an alanine residue at amino acid No. 15, and a leucine residue at amino acid No. 16 was synthesized. In order to improve solubility, the alanine residues at amino acid Nos. 6 and 15 were substituted by serine residues to synthesize A3-1(Opt2) peptide (SEQ ID NO: 44). The A3-1(Opt1) peptide and the A3-1(Opt2) peptide were evaluated for their affinity for hIgA and consequently determined to have 0.044 μM and 0.025 μM, respectively, demonstrating that the affinity was elevated by approximately 12 times and approximately 21 times, respectively, relative to that of A3-1.

Figure 14:
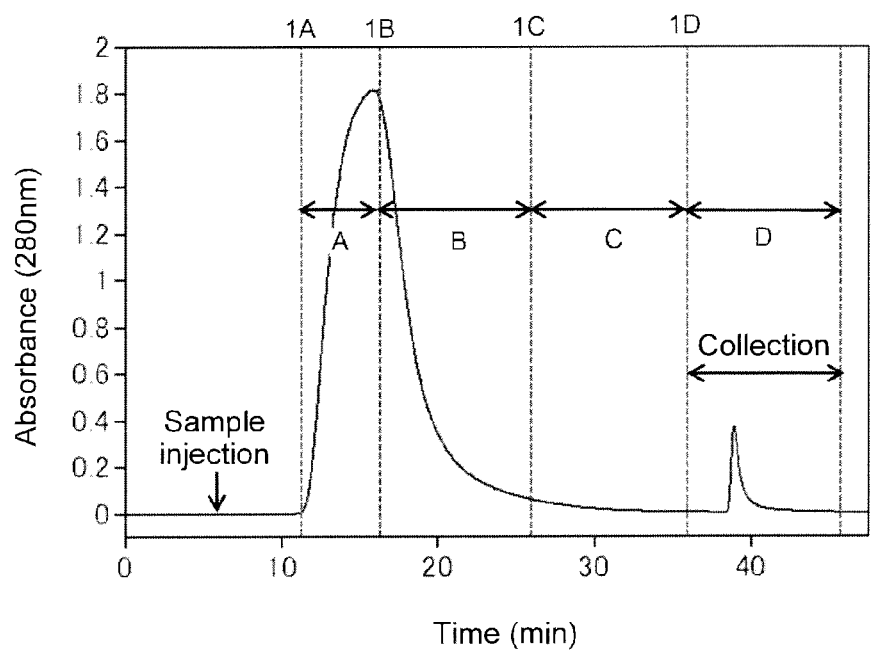
FIG. 14 shows the purification of IgA from human serum using a synthetic A3-1(Opt2) peptide-immobilized column.

In order to confirm the specificity of A3-1(Opt2) exhibiting the highest affinity, hIgA1 and hIgA2 were injected to an A3-1(Opt2)-immobilized sensor chip to perform surface plasmon resonance analysis using Biacore T100 (GE column was prepared, and hIgA was purified from human serum. One (1) ml of human serum was diluted 5-fold with PBS and then applied to the column connected with Profinia Protein Purification System (Bio-Rad). After washing with PBS, bound proteins were eluted with 0.2 M glycine-HCl (pH 2.5) (FIG. 14). More distinct peak was detected in an elution fraction, compared with the A-2 peptide column (FIG. 8). The improved affinity presumably increased the amount of hIgA adsorbed in the column.

INDUSTRIAL APPLICABILITY

The present invention provides a peptide capable of specifically or selectively binding to human IgA. This peptide is industrially useful for IgA purification in the production of IgA as an antibody drug and for analysis of IgA.

All publications, patents, and patent applications cited herein are incorporated herein by reference in their entirety.

Free Text for Sequence Listing
  SEQ ID NOs: 1 to 44: IgA-binding peptides
  SEQ ID NO: 45: DNA encoding IgA-binding peptide A-2

The invention claimed is:

1. A peptide which consists of any of the following amino acid sequences 1) to 7):
   1) QMRCLSYKGRRVCLWL (SEQ ID NO: 2),
   2) KRLCLQYKGSKVCFRL (SEQ ID NO: 4),
   3) RMRCLTYRGRRVCLEL (SEQ ID NO: 5),
   4) SMRCLQYRGSRVCLTL (SEQ ID NO: 6),
   5) HLRCLRYKGTRVCFSL (SEQ ID NO: 8),
   6) HVRCLSYKGREVCVQL (SEQ ID NO: 9), and
   7) PRMCLHYKGRRVCIPY (SEQ ID NO: 10),
wherein the peptide is capable of binding to human IgA, and wherein said peptide is optionally labeled, linked to a protein as part of a fusion protein, or bound to a solid phase.

2. The peptide according to claim 1, wherein the peptide has a disulfide bond between its two cysteine (C) residues.

3. The peptide according to claim 1, wherein the peptide is capable of binding to serum (monomeric) IgA and secretory (dimeric) IgA.

4. The peptide according to claim 1, wherein the peptide is labeled.

5. A fusion protein comprising a protein linked to a peptide according to claim 1.

6. An immobilized peptide comprising a peptide according to claim 1 bound to a solid phase.

7. A nucleic acid encoding a peptide according to claim 1.

8. A method for purifying IgA comprising binding IgA to
   A) a peptide which consists of any of the following amino acid sequences 1) to 7):
      1) QMRCLSYKGRRVCLWL (SEQ ID NO: 2),
      2) KRLCLQYKGSKVCFRL (SEQ ID NO: 4),
      3) RMRCLTYRGRRVCLEL (SEQ ID NO: 5),
      4) SMRCLQYRGSRVCLTL (SEQ ID NO: 6),
      5) HLRCLRYKGTRVCFSL (SEQ ID NO: 8),
      6) HVRCLSYKGREVCVQL (SEQ ID NO: 9), and
      7) PRMCLHYKGRRVCIPY (SEQ ID NO: 10),
   wherein the peptide is capable of binding to human IgA, or
   (B) an immobilized peptide according to claim 6; and releasing the bound IgA to collect the purified IgA.

9. A method for detecting IgA comprising binding IgA in a sample to
   A) a peptide that consists of any of the following amino acid sequences 1) to 7):
      1) QMRCLSYKGRRVCLWL (SEQ ID NO: 2),
      2) KRLCLQYKGSKVCFRL (SEQ ID NO: 4),
      3) RMRCLTYRGRRVCLEL (SEQ ID NO: 5),
      4) SMRCLQYRGSRVCLTL (SEQ ID NO: 6),
      5) HLRCLRYKGTRVCFSL (SEQ ID NO: 8),
      6) HVRCLSYKGREVCVQL (SEQ ID NO: 9), and
      7) PRMCLHYKGRRVCIPY (SEQ ID NO: 10),
   wherein the peptide is capable of binding to human IgA, or
   (B) an immobilized peptide according to claim 6; and detecting bound IgA.

10. A kit for analysis or purification of human IgA comprising
    (A) at least one peptide that consists of any of the following amino acid sequences 1) to 7):
       1) QMRCLSYKGRRVCLWL (SEQ ID NO: 2),
       2) KRLCLQYKGSKVCFRL (SEQ ID NO: 4),
       3) RMRCLTYRGRRVCLEL (SEQ ID NO: 5),
       4) SMRCLQYRGSRVCLTL (SEQ ID NO: 6),
       5) HLRCLRYKGTRVCFSL (HQ ID NO: 8),
       6) HVRCLSYKGREVCVQL (HQ ID NO: 9), and
       7) PRMCLHYKGRRVCIPY (HQ ID NO: 10),
    wherein the peptide is capable of binding to human IgA, or
    (B) an immobilized peptide according to claim 6.

11. A column for IgA separation, comprising an immobilized peptide according to claim 6.

12. A peptide consisting of any of the following amino acid sequences 1) to 7):
    1) QMRCLSYKGRRVCLWL (SEQ ID NO: 2),
    2) KRLCLQYKGSKVCFRL (SEQ ID NO: 4),
    3) RMRCLTYRGRRVCLEL (SEQ ID NO: 5),
    4) SMRCLQYRGSRVCLTL (SEQ ID NO: 6),
    5) HLRCLRYKGTRVCFSL (SEQ ID NO: 8),
    6) HVRCLSYKGREVCVQL (SEQ ID NO: 9), and
    7) PRMCLHYKGRRVCIPY (SEQ ID NO: 10),
wherein the peptide is capable of binding to human IgA.

* * * * *